US012569851B2

(12) United States Patent  (10) Patent No.: US 12,569,851 B2
Chou et al.  (45) Date of Patent: Mar. 10, 2026

(54) DIGITAL ASSAY

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 837 days.

(21) Appl. No.: 16/484,620

(22) PCT Filed: Feb. 8, 2018

(86) PCT No.: PCT/US2018/017489
§ 371 (c)(1),
(2) Date: Aug. 8, 2019

(87) PCT Pub. No.: WO2018/148458
PCT Pub. Date: Aug. 16, 2018

(65) Prior Publication Data
US 2020/0038859 A1     Feb. 6, 2020

Related U.S. Application Data

(60) Provisional application No. 62/621,475, filed on Jan. 24, 2018, provisional application No. 62/460,076, filed on Feb. 16, 2017, provisional application No. 62/460,062, filed on Feb. 16, 2017, provisional application No. 62/459,337, filed on Feb. 15, 2017, provisional application No. 62/457,133, filed on Feb. 9, 2017, provisional application No. 62/457,009, filed on Feb. 9, 2017, provisional application No. 62/456,603, filed on Feb. 8, 2017, provisional application No. 62/456,504, filed on Feb. 8, 2017.

(51) Int. Cl.
B01L 3/00       (2006.01)
C12Q 1/686      (2018.01)
G01N 33/53      (2006.01)

(52) U.S. Cl.
CPC .......... B01L 3/50851 (2013.01); C12Q 1/686 (2013.01); G01N 33/5308 (2013.01); B01L 2200/021 (2013.01); B01L 2200/0642 (2013.01); B01L 2200/0668 (2013.01); B01L 2200/16 (2013.01); B01L 2300/046 (2013.01); B01L 2300/0663 (2013.01); B01L 2300/0819 (2013.01); B01L 2300/0829 (2013.01); B01L 2300/0893 (2013.01); B01L 2300/12 (2013.01)

(58) Field of Classification Search
CPC .......... B01L 3/50851; B01L 3/50853
USPC .............. 422/552, 553
See application file for complete search history.

(56) References Cited

U.S. PATENT DOCUMENTS

| | | | |
|---|---|---|---|
| 3,368,872 A | 2/1968 | Natelson |
| 3,447,863 A | 6/1969 | Patterson |
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |

(Continued)

FOREIGN PATENT DOCUMENTS

| | | |
|---|---|---|
| AU | 619459 B | 1/1992 |
| EP | 0291153 B1 | 6/1992 |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

(Continued)

*Primary Examiner* — Natalia Levkovich

(57) ABSTRACT

Provided herein is a method and device for partitioning a fluidic sample. The device contains a plate containing microwells. The method comprises depositing a sample on one or both of the plates when the plates are in an open configuration, wherein the deposition is in the form of a single or multiple droplet of the sample, wherein at least one of the droplets has a volume that occupies more than two microwells and closing the plates to the closed configuration to partition the sample in the microwells.

45 Claims, 16 Drawing Sheets

(56) References Cited

U.S. PATENT DOCUMENTS

| | | | |
|---|---|---|---|
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0087033 A1* | 5/2004 | Schembri ............. B01L 3/5027 |
| | | 435/7.1 |
| 2004/0131345 A1 | 7/2004 | Kylberg et al. |
| 2004/0156755 A1 | 8/2004 | Levine |
| 2004/0191924 A1* | 9/2004 | Hunter ............... B01F 33/3021 |
| | | 506/40 |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |

(56) References Cited

U.S. PATENT DOCUMENTS

| | | |
|---|---|---|
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| EP | 0261667 B1 | 2/1993 |
| EP | 0961110 A2 | 12/1999 |
| EP | 2290100 B1 | 3/2011 |
| EP | 2439515 B1 | 4/2012 |
| EP | 3026433 A1 | 6/2016 |
| EP | 1949310 B1 | 2/2019 |
| WO | 1991020009 A1 | 12/1991 |
| WO | 1999044743 A1 | 9/1999 |
| WO | 1999045385 A1 | 9/1999 |
| WO | 2003062920 A2 | 7/2003 |
| WO | 2005114145 A2 | 12/2005 |
| WO | 2005100539 A2 | 1/2006 |
| WO | 2007112332 A2 | 10/2007 |
| WO | 2009117652 A1 | 9/2009 |
| WO | 2009117664 A2 | 9/2009 |
| WO | 2009117678 A1 | 9/2009 |
| WO | 2009117682 A1 | 9/2009 |
| WO | 2009124186 A1 | 10/2009 |
| WO | 2009124190 A1 | 10/2009 |
| WO | 2009126800 A1 | 10/2009 |
| WO | 2010115026 A1 | 10/2010 |
| WO | 2014055559 A1 | 4/2014 |
| WO | 2014089468 A1 | 6/2014 |
| WO | 2014183049 A1 | 11/2014 |
| WO | 2014205576 A1 | 12/2014 |
| WO | 2017048871 A1 | 3/2017 |

OTHER PUBLICATIONS

Search and Written Opinion for PCT/US2018/017489 established by ISA/KR, mailed on May 31, 2018.

* cited by examiner (The diffusion time of analyte from one well to other is much longer than the incubation time. Since the distance between each well is larger than the well depth)

b. Representative photo in amplification step a. Representative photo in capture step Amplicons

DIGITAL ASSAY

CROSS-REFERENCING

This application is a § 371 national stage application of International Application PCT/US2018/017489 filed on Feb. 8, 2018, which claims the benefit of priority to provisional application Ser. No. 62/457,009 filed on Feb. 9, 2017 (ESX-040PRV), 62/460,076 filed on Feb. 16, 2017 (ESX-040PRV2), 62/621,475 filed on Jan. 24, 2018 (ESX-040PRV3), 62/456,603 filed on Feb. 8, 2017 (ESX-033PRV), 62/459,337 filed on Feb. 15, 2017 (ESX-033PRV2), 62/456,504 filed on Feb. 8, 2017 (ESX-045PRV), 62/460,062 filed on Feb. 16, 2017 (ESX-045PRV2) and 62/457,133 filed on Feb. 9, 2017 (ESX-046PRV), the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays.

BACKGROUND

Among other things, the present invention provides devices and methods that allow assaying of an analyte in a sample more accurate, simpler, and faster than certain prior arts. In certain embodiments, the present invention compartments a sample into isolated or nearly isolated microwells that has a predetermined geometry and volume, and a cover plate to isolate or nearly isolate the samples in each wells from its neighboring wells. The present invention can be used for digital PCR (polymerase chain reaction).

SUMMARY

A device for performing a digital assay is provided, comprising: a first plate, a second plate, and microwells, wherein: (a) the first and second plates are movable relative to each other into different configurations, and have, on its respective surface, a sample contact area for contacting the fluidic sample that containing an analyte; (b) the second plate has, in the sample contact area, a plurality of the microwells, wherein each microwell has (i) predetermined and known geometry, (ii) a well depth of 200 um or less, and (iii) has a volume substantially less than that of the fluidic sample, wherein one of the configurations is an open configuration, in which: the average spacing between the inner surface of the first plate and the rim of the microwells in the second plate is larger than the depth of the well and the sample is deposited on one or both of the plates; and wherein another of the configurations is a closed configuration, which is the configuration after the sample is deposited in the open configuration; in the closed configuration, at least a part of the sample is inside the microwells, and the average spacing between the inner surface of the first plate and the rim of the microwell in the second plate is less than 1 um or less than ¹⁄₁₀ (one tenth) of the microwell depth.

A method for partitioning a fluidic sample, comprising: obtaining a device or apparatus of any of any prior claim, depositing a sample on one or both of the plates when the plates are in an open configuration, wherein the deposition is in the form of a single or multiple droplet of the sample, wherein at least one of the droplets has a volume that occupies more than two microwells; and closing the plates to the closed configuration to partition the sample in the microwells.

BRIEF DESCRIPTION OF THE DRAWINGS

The skilled artisan will understand that the drawings, described below, are for illustration purposes only. The drawings are not intended to limit the scope of the present teachings in any way. The drawings not are not entirely in scale. In the figures that present experimental data points, the lines that connect the data points are for guiding a viewing of the data only and have no other means.

In FIG. 4 the QMAX device is in an open configuration. (a) A device comprising a first plate, a second plate, and microwells on second plate. (b) Top view of microwells on second plate with (i) round shape with square lattice (ii) rectangle shape with square lattice (iii) triangle shape with hexagonal lattice (iv) round shape with aperiodicity.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

A. Principle of Microwell Array Pixelated Assays (MAPA)

Figure 4:
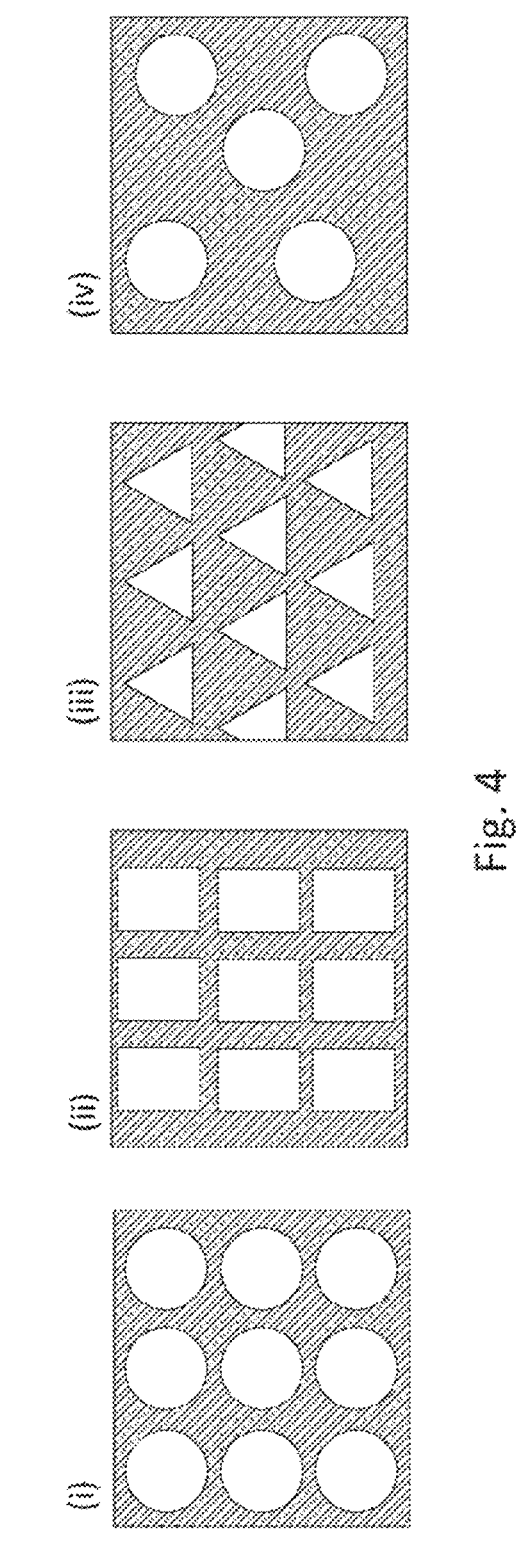
FIG. 4 is a schematic drawing for an exemplary embodiment of a pixelated assay QMAX device (Q: quantification; M: magnifying; A: adding reagents; X: acceleration; also known as compressed regulated open flow (CROF)) device that can be used for pixelated assay.

GD1 As illustrated in FIG. 4, a device for pixelated assay using microwell array, termed MAPA or "microwell array pixelated assay", comprising a first plate, a second plate, and microwells;

(a) the first and second plates are movable relative to each other into different configurations, and have, on its respective surface, a sample contact area for contacting the fluidic sample;

(b) the second plate has, in the sample contact area, a plurality of the microwells, wherein each microwell has (i) predetermined and known geometry, (ii) a well depth of 200 um or less, and (iii) has a volume substantially less than that of the fluidic sample, wherein one of the configurations is an open configuration, in which: the average spacing between the inner surface of the first plate and the rim of the microwells in the second plate is larger than the depth of the well and the sample is deposited on one or both of the plates; and wherein another of the configurations is a closed configuration, which is the configuration after the sample is deposited in the open configuration; in the closed configuration, at least a part of the sample is inside the microwells, and the average spacing between the inner surface of the first plate and the rim of the microwell in the second plate is less than 1 um or less than $\frac{1}{10}$ (one tenth) of the microwell depth.

GM1. A method for pixelated assaying a fluidic sample comprising:

i. obtaining a first plate, ii. obtaining a second plate, wherein (a) the first and second plates are movable relative to each other into different configurations, and have, on its respective surface, a sample contact area for contacting a fluidic sample that contains a target analyte;

(b) the second plate has, in the sample contact area, a plurality of the microwells, wherein each microwell has (i) a well depth of 200 um or less, and (ii) a well that ha a volume substantially less than that of the sample;

iii. depositing a sample on one or both of the plates when the plates are in an open configuration; and iv. making the plates into a closed configuration;

wherein the open configuration is the configuration, in which: the average spacing between the inner surface of the first plate and the rim of the microwells in the second plate is larger than the depth of the well and the sample is deposited on one or both of the plates;

wherein the closed configuration is the configuration, which is the configuration after the sample is deposited in the open configuration; in the closed configuration, at least a part of the sample is inside the microwells, and the average spacing between the inner surface of the first plate and the rim of the microwell in the second plate is less than 1 um or less than $\frac{1}{10}$ (one tenth) of the microwell depth.

In the method of any prior embodiments, wherein it further comprises a step of measuring, while the plates are in a closed configuration, the signal related to analytes.

In the device or method of any prior embodiments, wherein further a sealing layer is on the inner surface of either one or both of the plates, wherein the sealing layer is configured that when the plate is in a closed configuration, the sealing layer prevent a liquid from one well to its neighboring well. An example of the sealing layer is a thin adhesive layer.

In the device or method of any prior embodiments, wherein the analyte is a molecule. In some embodiments, the analyte is a protein and/or nucleic acids (e.g. DNA or RNA). In some embodiments the analyte is a small molecule.

In the device or method of any prior embodiments, wherein further a binding site is either on the inner surface of one or both of the plates, wherein the binding site comprises a capture agent immobilized at the site, and the capture agent is configured to specifically capture the analyte.

In the device or method of any prior embodiments, wherein further a storage site is either on the inner surface of one or both of the plates, wherein the storage site comprises a reagent at the site, and the reagent can be dissolved into a liquid.

In the method of any prior embodiments, wherein it further has a step of amplification, wherein the amplification makes the analyte more observable than that without the amplification, and wherein the analyte signal amplification in a well includes, but not limited, chemical reactions or physical enhancements (e.g. plasmonic structures) or both. Examples include, but not limited to, (a) for nucleic acids, various types PCR (polymerase chain reaction), LAMP (Loop-mediated isothermal amplification), etc., (b) for proteins, ELISA (enzyme-linked immunosorbent assay), light enhancement using plasmonic structures (e.g. plasmonic metal structures), and (c) for small molecules, chemical reactions. The chemical reactions include, but not limited to, chemiluminescence or other luminescence.

In the method of any prior embodiments, wherein it further has steps of subtracting air-pockets in determining the actual sample volume, by (i) identifying the empty wells by imaging wells in a bright field image and/or by imaging before the amplification step, and (ii) subtracting the empty well in volume calculation in quantify the analyte concentration.

Figure 1:
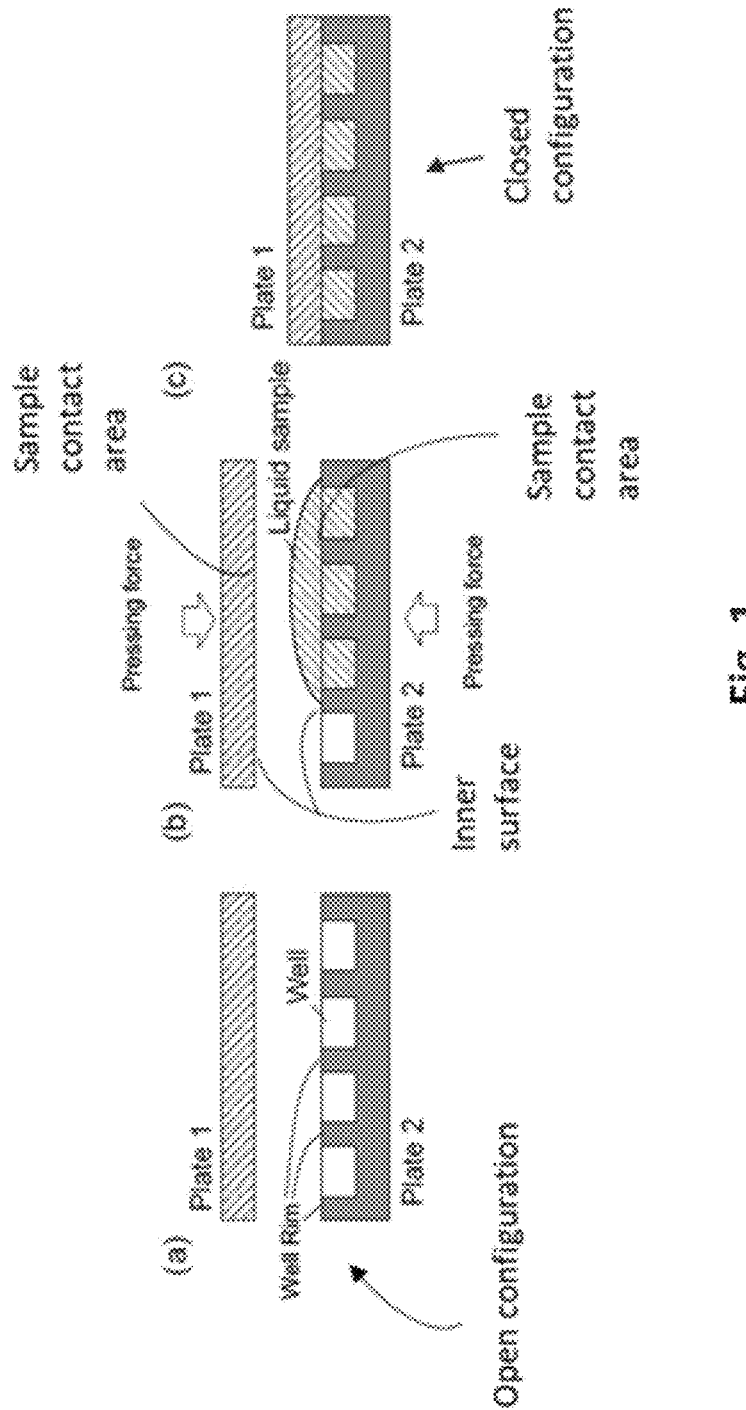
FIG. 1 (a) Schematics of two plates: plate 1 has a flat inner surface, and plate 2 has a well array on its sample contact surface. (b) Depositing sample liquid at the center of the well array plate (plate 2), covering with the flat plate (plate 1) and pressing the two plates together. (c) The liquid are separated into well array after pressing.
Figure 2:
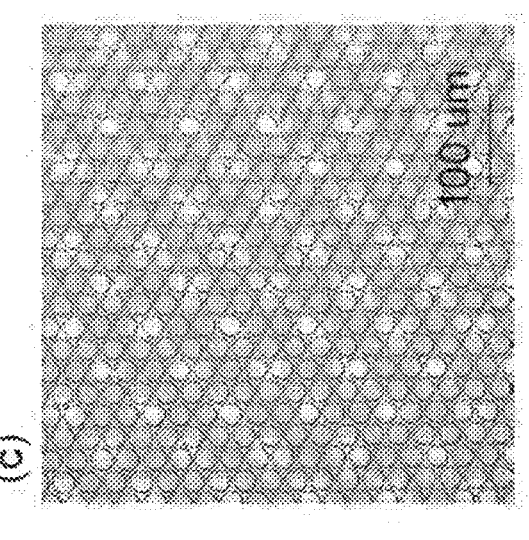
FIG. 2 (a) Photograph of microwell plate fabricated on 175 um thick PMMA substrate; (b) microscopy photo of microwell array in hexagonal lattice with well diameter of 30 um, well depth of 8 um and well center to center distance of 34 um; (c) microscopy photo of micro well array in hexagonal lattice with well diameter of 20 um, well depth of 8 um and well center to center distance of 24 um.
Figure 2:
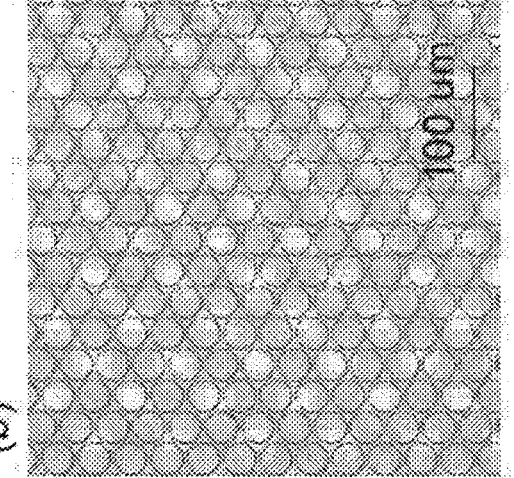
Figure 2:
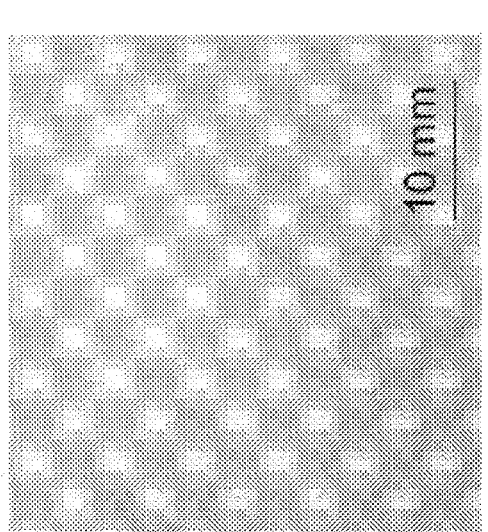
Figure 3:
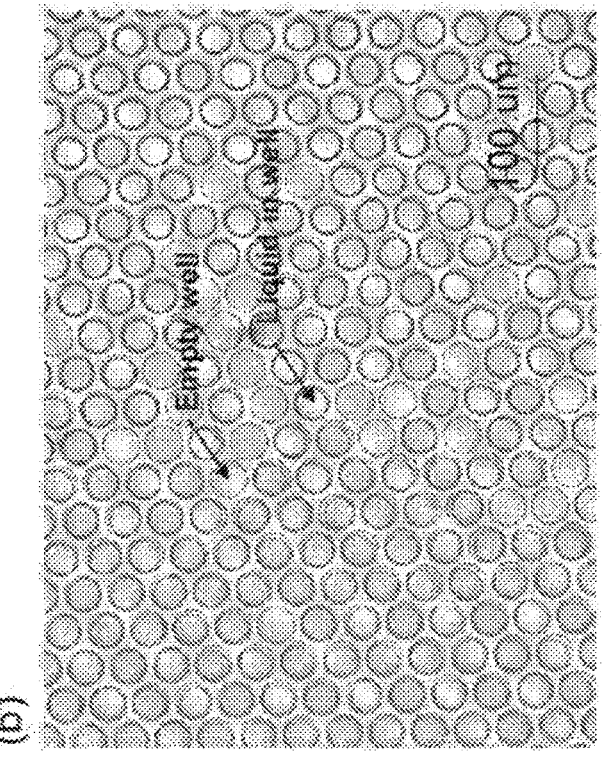
FIG. 3 Microscopy photos with (a) 10× magnification and (b) 20× magnification of liquid separated into well array after pressing (with human fingers) the two plates together (microwell plates and flat plate as described in FIG. 1). In the setup, plate 1 (flat plate) is a flat PET film with a thickness of 50 um, and plate 2 (microwell plate) is a PMMA plate with a thickness of 175 um and a micro array on surface in hexagonal lattice with well diameter of 30 um, well depth of 8 um and well center to center distance of 34 um. The liquid is 2 uL volume phosphate-buffered saline (PBS). Note that after depositing a liquid sample and bring the plates into a closed configuration, some of the microwells are filled while some of the microwells are empty. Our measurements show that in closed configuration of the plates, there is a thin residue layer of liquid (~0.5 um thick or less) between the plate 1 inner surface and the rim of the wells on the plate.
Figure 3:
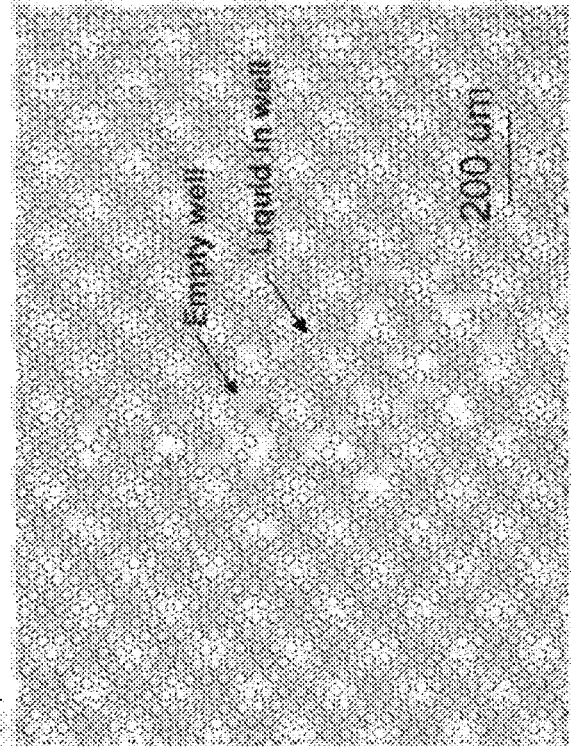

FIGS. 1-3 schematically illustrate some principles of an embodiment of this method.

Spacers

In certain embodiments of the present invention, the device in prior embodiments further comprise spacers that are configured to keep the distance between the inner surface of the first plate and the well bottom substantially uniform (i.e. substantially the same over the entire well). In some embodiments, the spacers are fixed inside the wells, or on the inner surface of the first plate, or both. Examples of the spacers are described in Nos. PCT/US2016/045437 and PCT/US0216/051775, which were respectively filed on Aug. 10, 2016 and Sep. 14, 2016, which are incorporated herein in their entireties for all purposes.

Pixelated Assaying for Samples with a Low Analyte Concentration

For a given analyte concentration (particularly at a low concentration), the volume of each well of can be configured, so that a well has either one analyte or no analyte. In this case, one can amplify, when the plates are in a closed configuration, a signal related to the analyte in a well (that has an analyte) without being affected or significantly affected by other wells.

After an amplification of analyte signal, one can detect an analyte by checking the existence of the wells that have an observable signal related to the analyte. By counting the number of wells that have an observable signal related to the analyte and by determining the related sample volume using the plates, the concentration of the analyte in the sample can be determined.

In assaying a low analyte concentration sample, each well can be viewed at a pixel and one determines the analyte concentration by counting the number of pixels that have signal. Such assays are also termed digital assay.

The volume of a sample can be determined by the well volume and number of wells and the sample occupation inside the well.

B. Pixelated Detection of Nucleic Acids

In the device or method of any prior embodiments, wherein the analyte is a nucleic acid, and the device, or method is configured to conduct nucleic acid amplification techniques include but not limited to, different polymerase chain reaction (PCR) methods, such as hot-start PCR, nested PCR, touchdown PCR, reverse transcription PCR, RACE PCR, digital PCR, real-time PCR, etc., and isothermal amplification methods, such as loop-mediated isothermal amplification (LAMP), strand displacement amplification, helicase-dependent amplification, nicking enzyme amplification, rolling circle amplification, recombinase polymerase amplification, etc.

Digital polymerase chain reaction (digital PCR, DigitalPCR, dPCR, or dePCR) can be used to directly quantify and clonally amplify nucleic acids strands including DNA, cDNA or RNA. The key difference between dPCR and traditional PCR lies in the method of measuring nucleic acids amounts, with the former being a more precise method than PCR, though also more prone to error in the hands of inexperienced users.[1]:217 A "digital" measurement quantitatively and discretely measures a certain variable, whereas an "analog" measurement extrapolates certain measurements based on measured patterns. PCR carries out one reaction per single sample. dPCR also carries out a single reaction within a sample, however the sample is separated into a large number of partitions and the reaction is carried out in each partition individually. This separation allows a more reliable collection and sensitive measurement of nucleic acid amounts. The method has been demonstrated as useful for studying variations in gene sequences—such as copy number variants and point mutations—and it is routinely used for clonal amplification of samples for next-generation sequencing.

dPCR improves upon the current PCR practices by dividing up the reaction into multiple, smaller reactions. A sample is partitioned so that individual nucleic acid molecules within the sample are localized and concentrated within many separate regions. Micro well plates, capillaries, oil emulsion, and arrays of miniaturized chambers with nucleic acid binding surfaces can be used to partition the samples. A PCR solution is made similarly to a TaqMan assay, which consists of template DNA (or RNA), fluorescence-quencher probes, primers, and a PCR master mix, which contains DNA polymerase, dNTPs, MgCl2, and reaction buffers at optimal concentrations. The PCR solution is divided into smaller reactions and are then made to run PCR individually. After multiple PCR amplification cycles, the samples are checked for fluorescence with a binary readout of "0" or "1". The fraction of fluorescing droplets is recorded. The partitioning of the sample allows one to estimate the number of different molecules by assuming that the molecule population follows the Poisson distribution, thus accounting for the possibility of multiple target molecules inhabiting a single molecule. Using Poisson's law of small numbers, the distribution of target molecule within the sample can be accurately approximated allowing for a quantification of the target strand in the PCR product. A Poisson distribution of the copies of target molecule per droplet (CPD) based on the fraction of fluorescent droplets (p), represented by the function $CPD=-\ln(1-p)$. This model simply predicts that as the number of samples containing at least one target molecule increases, the probability of the samples containing more than one target molecule increases. In conventional PCR, the number of PCR amplification cycles is proportional to the starting copy number. dPCR, however, is not dependent on the number of amplification cycles to determine the initial sample amount, eliminating the reliance on uncertain exponential data to quantify target nucleic acids and therefore provides absolute quantification.

In the device or method of any prior embodiments, wherein the device is further configured to conduct fast thermal cycling in PCR, wherein the configuration includes, but not limited to, heaters and coolers to be added onto the device or next to the devices as well as other additional devices, materials and/or methods, which are disclosed in U.S. Provisional Application No. 62/456,596, which was filed on Feb. 8, 2017, U.S. Provisional Application No. 62/456,504, which was filed on Feb. 8, 2017, and U.S. Provisional Application No. 62/459,496, which was filed on Feb. 15, 2017, U.S. Provisional Application No. 62/488,684, which was filed on Apr. 21, 2017, U.S. Provisional Application No. 62/510,063, which was filed on May 23, 2017, all of which applications are incorporated herein in their entireties for all purposes.

Figure 11:
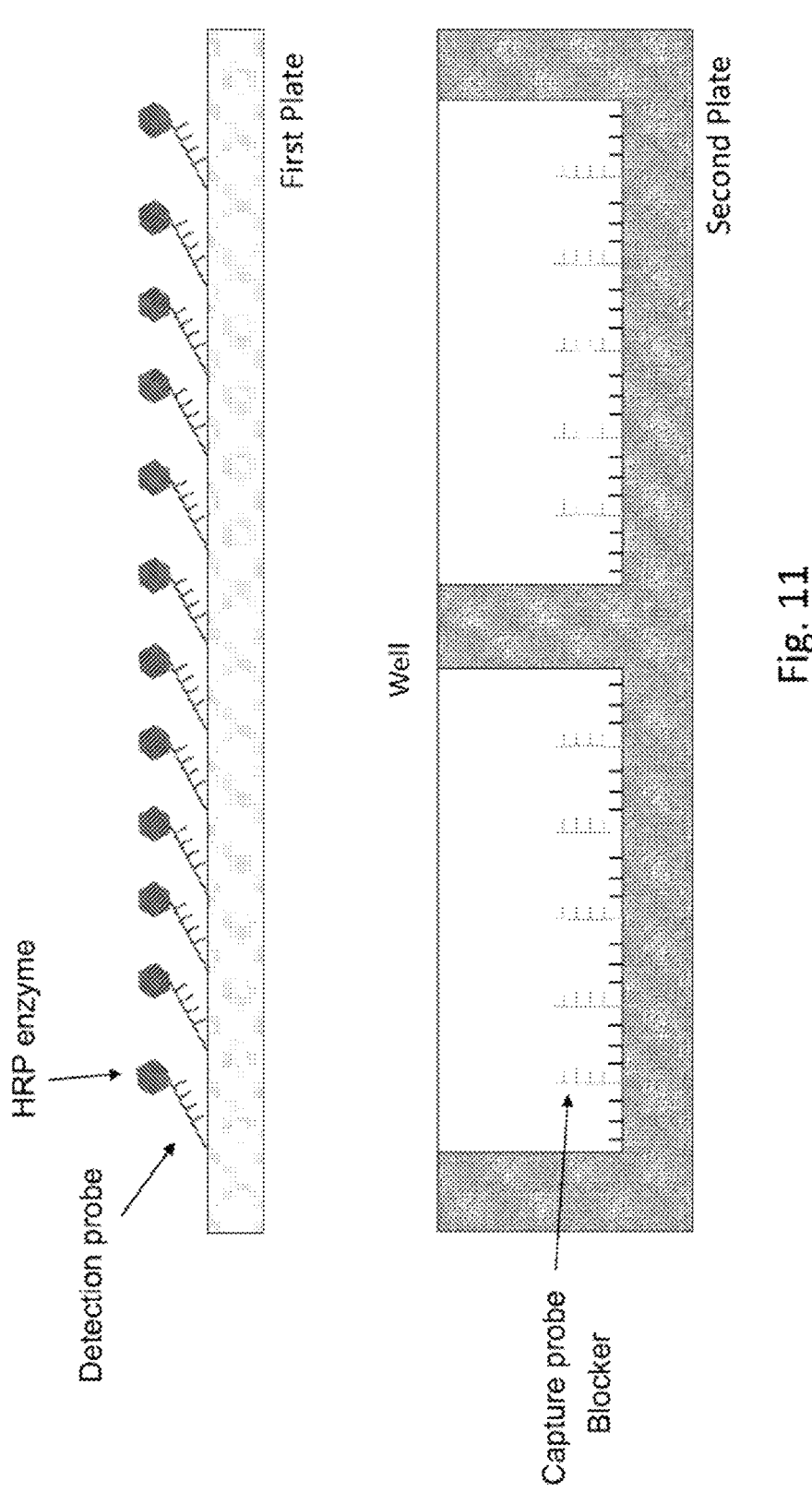
FIG. 11 shows schematics of preparation of binding site plate (first plate) and storage plate (second plate) of an exemplary embodiment for pixelated assay QMAX. The experiment process follows the flow chart of FIG. 5.

FIG. 11 shows schematics of preparation of binding site plate (first plate) and storage plate (second plate) of an exemplary embodiment for pixelated assay QMAX. The experiment process follows the flow chart of FIG. 5.

Specifically, the first plate in this example is square-well array with size of 20 um by 20 um, period of 100 um, depth of 30 um fabricated on 0.25 mm thick acrylic substrate. The substrate was first treated with 1M sodium hydroxide at 45° C. for 2 hours followed by rinsing with water for 3 times. The substrate was then coated with 8 mg/ml EDC and 11.2 mg/ml NHS in MES buffer (pH 4.7) at room temperature for 2 hours. 20 ug/ml of streptavidin was then coated on the first plate at room temperature for 2 hours, followed by rinsing with PBS for 3 times. The substrate was then blocked with 4% BSA at room temperature for 1 hour, followed by rinsing with PBS for 3 times. 1 uM of biotinylated capture probe was coated on the first plate at room temperature for 2 hours, followed by washing three times with PBST. Excessive liquid was removed and the plate was dried at room temperature.

The second plate in this example is a flat 0.175 mm thick acrylic film. 200 ul of 1 uM detection probe conjugated with HRP was uniformly printed and dried on the second plate at 37° C. for 2 hours.

As shown in FIG. 11, in some embodiments the first plate comprises a capture probe that is fully or partially coated on the inner surface of the first plate. In some embodiments the capture probe is fully or partially on the bottom or side wall or both of the well on the first plate.

In some embodiments, the capture probe can be applied to the surface by printing, spraying, soaking or any other method that applies homogenous or partial layer of reagents. In certain embodiments, the capture probe is directly coated on the first plate. It should also be noted that in some embodiments the capture probe is coated on the inner surface of the first plate, not the second plate; in some embodiments the capture probe is coated on the inner surface of the second plate, not the first plate; in some embodiments the capture probe is coated on the inner surfaces of both plates. In some embodiments, the concentration of coated capture probe ranges from 1 fM to 1 mM.

In some embodiments, capture probe is usually 10-50 bp in length, and 3' end modified to facilitate coating on the substrate. Commonly used 3' end modifications include but not limited to thiol, dithiol, amine, biotin, etc. Substrates can be used for capture probe immobilization include but not limited to acrylic film, gold surface, PS, etc.

As shown in FIG. 11, in some embodiments the first plate comprises blockers that are coated on the inner surface of the first plate. In some embodiments, the blockers block any unoccupied sites on the solid surface that can cause unwanted nonspecific bindings in assays. In certain embodiments, the blocker reduces nonspecific binding. In certain embodiments, the blockers can be applied to the surface by printing, spraying, soaking or any other method that applies homogenous layer of reagents. In certain embodiments, the blockers are dried on the first plate. It should also be noted that in some embodiments the blockers are coated on the inner surface of the first plate, not the second plate; in some embodiments the blockers are coated on the inner surface of the second plate, not the first plate; in some embodiments the blockers are coated on the inner surfaces of both plate. In some embodiments, the blockers are bovine serum albumin (BSA), casein or total proteins from whole milk, etc. In some embodiments, the blockers are small molecules, such as 6-Mercapto-hexanol.

As shown in FIG. 11, in some embodiments the first plate comprises a stabilizer that is coated on the inner surface of the first plate. In some embodiments, the stabilizer helps maintain the proper folding of protein when dried so that the function of the protein is not disrupted during storage. In certain embodiments, the stabilizer prolongs the usage life span of the reagents, such as but not limited to a protein. In certain embodiments, the stabilizer can be applied to the surface by printing, spraying, soaking or any other method that applies homogenous layer of reagents. In certain embodiments, the stabilizer is dried on the first plate. It should also be noted that in some embodiments the stabilizer is coated on the inner surface of the first plate, not the second plate; in some embodiments the stabilizer is coated on the inner surface of the second plate, not the first plate; in some embodiments the stabilizer is coated on the inner surfaces of both plates. In some embodiments, the stabilizer is sugar such as but not limited to sucrose and glucose. In some embodiments, the stabilizer is a polymer. In certain embodiments, the stabilizer is glycerol.

As shown in FIG. 11, in some embodiments the second plate comprises a detection probe that is coated on the inner surface of the second plate. In some embodiments, the detection probe can be applied to the surface by printing, spraying, soaking or any other method that applies homogenous layer of reagents. In certain embodiments, the detection probe is dried on the second plate. It should also be noted that in some embodiments the detection antibody is coated on the inner surface of the second plate, not the first plate; in some embodiments the detection antibody is coated on the inner surface of the first plate, not the second plate; in some embodiments the detection probe is coated on the inner surfaces of both plates. In some embodiments, the concentration of coated detection probe ranges from 1 fM to 1 mM.

In some embodiments, the detection probe is configured to produce a detectable signal after binding to the nucleic acid target. For example, in some embodiments the signal can be a colorimetric signal, a luminescent signal, or a fluorescent signal. In some embodiments for example, the detection probe is labeled by a fluorescent label, which produces a signal after the detection probe binds to the nucleic acid target or to the capture probe-target complex. In some embodiments, the fluorescent label directly labels the detection probe. In some embodiments, the fluorescent label labels a reagent that can bind to the detection probe or a detection probe-target complex. In some embodiments, the detection probe is configured to a chemical that can amplified signal or the signal from this chemical can be amplified; wherein amplification method in this amplification step including, but not limit to:

The color based enzymatic reaction, the absorption signal generated by substrates are amplified by enzyme which are linked to the detection reagents; wherein the enzyme including but not limited to horseradish peroxidase and alkaline phosphatase; wherein the substrates including ABTS or TMB;

The fluorescence based enzymatic reaction, the fluorescence signal generated by substrates are amplified by enzyme which are linked to the detection reagents; wherein the enzyme including horseradish peroxidase and alkaline phosphatase; wherein the substrates including but not limited to Amplex red;

The chemiluminescent based enzymatic reaction, the chemiluminescent signal generated by substrates are amplified by enzyme which are linked to the detection reagents; wherein the enzyme including horseradish peroxidase and alkaline phosphatase; wherein the substrates including but not limited to luminol and isoluminal;

In some embodiments, examples of commonly used labeled enzymes and chromogenic or fluorogenic or chemiluminescent substrates are summarized in Table 1.

TABLE 1

Examples of labeled enzymes and substrates

| Labeled enzymes | Types | Substrates |
|---|---|---|
| Peroxidase | Chromogenic | TMB, ABTS, OPD, CN, AEC, DAB, TACS, SG, AEC, ImmPACT SG, VIP, NovaRED, ImmPACT AEC, ImmPACT VIP, ImmPACT AMEC Red, ImmPACT NovaRED, ImmPACT DAB, ImmPACT DAB EqV, Steady DAB, StayYellow, StayBlack |
| | Fluorogenic | ADHP, Amplex Red, Resazurin |
| | Chemiluminescent | Luminol, IsoLuminol, UptiLight, |
| Alkaline Phosphatase | Chromogenic | pNPP, INT, AP-Blue, Vector Red, Vector Blue, BCIP/NBT, Vector Black, ImmPACT Vector Red, StayRed, StayGreen, StayBlue, |
| | Fluorogenic | MUP, FPD |
| | Chemiluminescent | VisiGlo |
| Osidase | Chromogenic | X-Gal, ONG, MUG |
| | Fluorogenic | MUG |

Catalytic amplification. An analyte activates a catalyst, which then produces multiple copies of a reporter molecule.

Catalytic self-amplification. An analyte activates a catalyst, which results in the production of reporter molecules. These not only generate a signal, but are also able to activate the catalyst.

Analyte-induced modification of a collective property. The binding of a single analyte molecule to a receptor affects the properties of neighboring units through signal transduction.

Multivalent surfaces for binding of multiple analyte molecules. Recruitment of multiple reporters using multivalent scaffolds such as polymers, dendrimers or nanoparticles amplifies the signal.

Wherein above catalysts including Pd(0)-catalyst, apyrase, potassium permanganate, platinum, etc.

Figure 12:
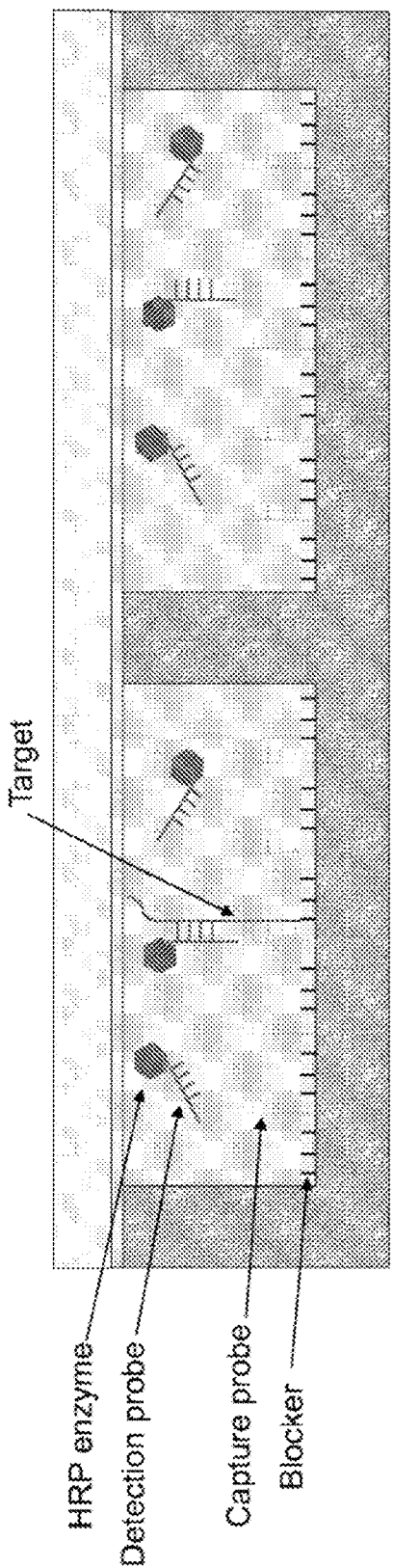
FIG. 12 shows a schematic drawing for an exemplary embodiment of a pixelated assay QMAX device in a closed configuration for capturing process

FIG. 12 shows a schematic drawing for an exemplary embodiment of a pixelated assay QMAX device in a closed configuration for capturing process. In this process, 1) Drop 1 uL sample containing nucleic acid target with concentrations of 1 aM to 1 mM on first plate
2) Press the second plate on top of the liquid by hand.
3) Take the photo of wells on first plate. The volume of total sample is calculated by counting the well filled with sample.
4) Incubate for 1 min.
5) Peel off the second plate/Wash the first plate with 5× SSC for 3 times.

As used herein, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

As used herein, the term "capture probe" refers to nucleic acid that hybridizes to nucleic acid having a complementary sequence.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

In some embodiments, hybridization reagents facilitate the hybridization between two nucleic acid complementary sequences, herein including but not limited to sodium chloride, sodium acetate, ficoll, dextran, polyvinylpyrrolidone, bovine serum albumin, etc.

In certain embodiments, the predetermined period of time is equal to or longer than the time needed for the target nucleic acids to diffuse into the sample across the layer of uniform thickness.

In certain embodiments, the predetermined period of time is equal to or longer than the time needed for the target nucleic acids.

Figure 13:
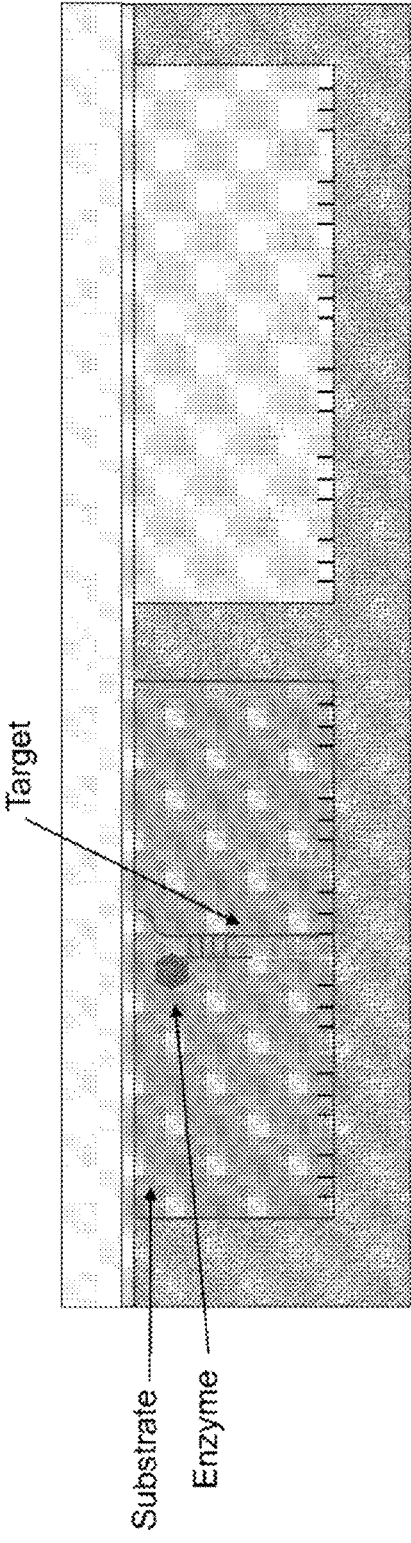
FIG. 13 shows a schematic drawing for an exemplary embodiment of a pixelated assay QMAX device in a closed configuration for amplification process.
Figure 14:
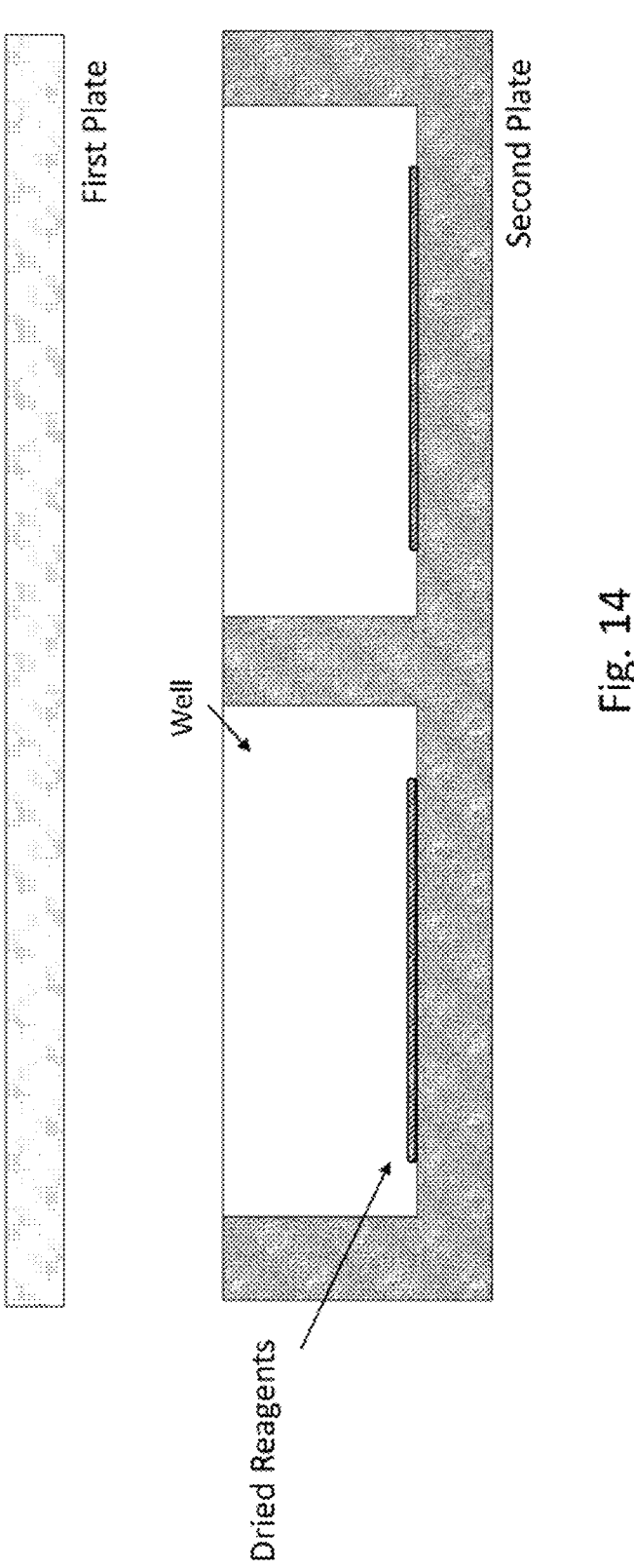
FIG. 14 shows a schematic drawing for an exemplary embodiment of a pixelated assay QMAX device in an open configuration for digital nucleic acid amplification assay.

FIG. 13 shows a schematic drawing for an exemplary embodiment of a pixelated assay QMAX device in a closed configuration for amplification process. In this process, 1) Drop 3 uL (over amount) TMB amplification substrate on first plate;
2) Press the amplification second plate on top of the liquid by hand;
3) Incubate for 1 min. In this process, only the well captured target gets amplified and show signal (color or fluorescence);
4) Take the photo of wells on first plate, and the count the number of wells with signals FIG. 14 shows a schematic drawing for an exemplary embodiment of a pixelated assay QMAX device in an open configuration for digital nucleic acid amplification assay.

In some embodiments, dried reagents include cell lysing reagents, which include but not limited to, salts, detergents, enzymes, and other additives. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions.

In some embodiments, "dried reagents" include PCR reagents, which include but not limited to, primers, deoxynucleotides (dNTPs), bivalent cations (e.g. $Mg2+$), monovalent cation (e.g. $K+$), buffer solutions, enzymes, and reporters. As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

In some embodiments, "dried reagents" include stabilizers, which include but not limited to protein stabilizers, examples include but not limited to polyols, sugars, amino acids, amines, and salting out salts; polymers and proteins, examples include but not limited to PEGs, polysaccharides, dextran, hydroxyl ethyl starch (HETA), PEG-4000, and gelatin; surfactants, examples include but not limited to Tween 20, Tween 80, Triton X-100, Brij 35, Pluronic F127, and SDS; amino acids, examples include but not limited to histidine, arginine, and glycine; preservatives, examples include but not limited to benzyl alcohol, m-cresol, and phenol.

Figure 15:
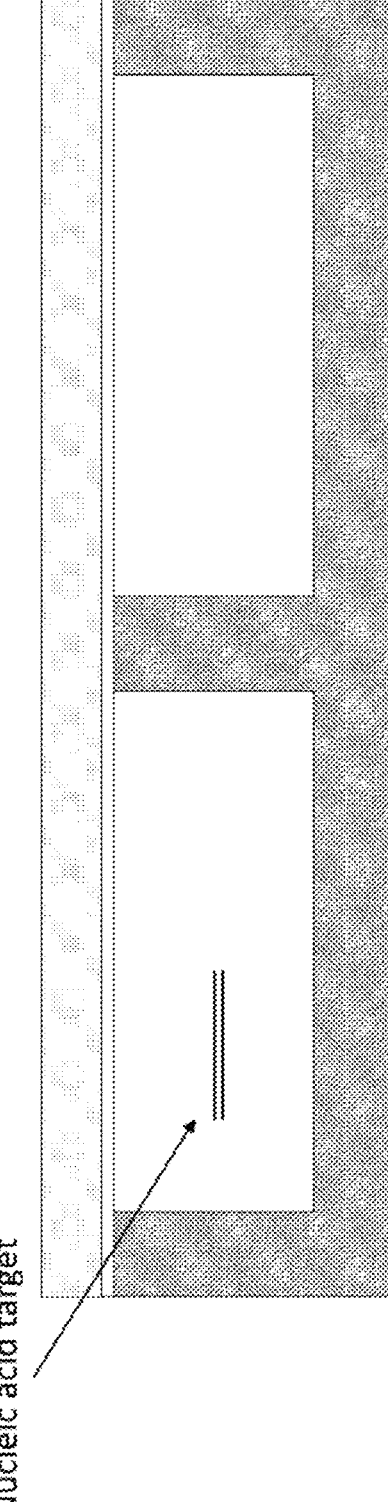
FIG. 15 shows a schematic drawing for an exemplary embodiment of a pixelated assay QMAX device in a closed configuration after sample introduction for digital nucleic acid amplification assay

FIG. 15 shows a schematic drawing for an exemplary embodiment of a pixelated assay QMAX device in a closed configuration after sample introduction for digital nucleic acid amplification assay. In this process, 1) Drop sample containing nucleic acid target on first plate
2) Press the second plate on top of the liquid by hand.
3) Take the photo of wells on first plate. The volume of total sample is calculated by counting the well filled with sample.

In some embodiments, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA, miRNA, and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

In some embodiment, after sample introduction, dried reagents in FIG. 14 are dissolved in the sample.

Figure 16:
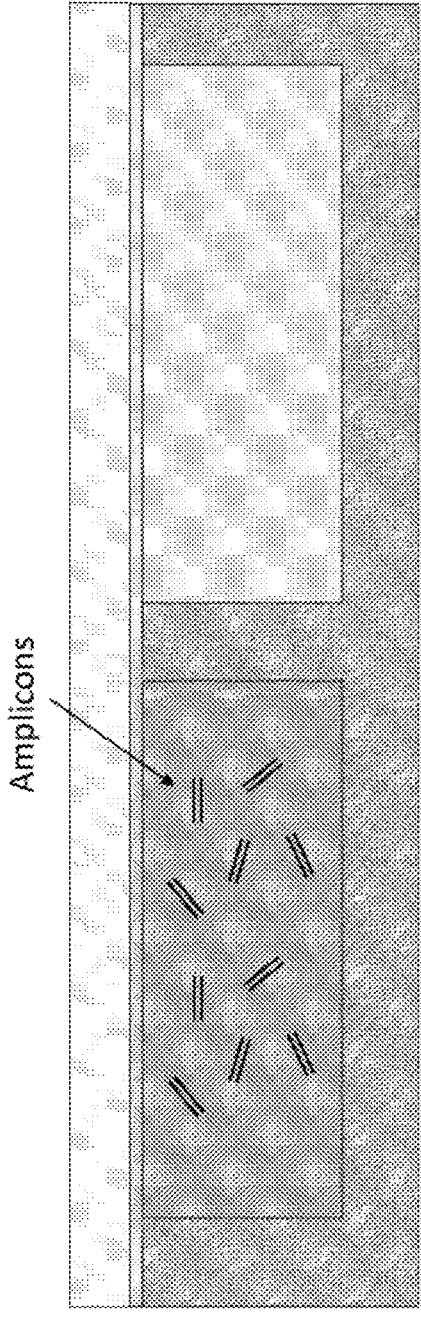
FIG. 16 shows a schematic drawing for an exemplary embodiment of a pixelated assay QMAX device in a closed configuration during digital nucleic acid amplification process.

FIG. 16 shows a schematic drawing for an exemplary embodiment of a pixelated assay QMAX device in a closed configuration during digital nucleic acid amplification process.

As used herein, "amplicon" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

C. Another Example of QMAX Device for Nucleic Acid Capturing for Hybridization Assays FIG. 4 is a schematic drawing for an exemplary embodiment of a QMAX (Q: quantification; M: magnifying; A:

adding reagents; X: acceleration; also known as compressed regulated open flow (CROF)) device that can be used for capturing nucleic acid for hybridization assays, for example. In FIG. 4 the QMAX device is in an open configuration.

DD1 A device for pixelated assaying a fluidic sample comprising:
    a first plate, a second plate, and microwells, wherein
    (a) the first and second plates are movable relative to each other into different configurations, and have, on its respective surface, a sample contact area for contacting a fluidic sample that contains a target analyte;
    (b) the second plate has, in the sample contact area, a plurality of the microwells, wherein each microwell has (i) a well depth of 200 um or less, (ii) a well that has a volume substantially less than that of the sample, and (iii) a binding site that comprises a capture agent immobilized at the site, and the capture agent is configured to capture the target analyte;
    wherein one of the configurations is an open configuration, in which: the average spacing between the inner surface of the first plate and the rim of the microwells in the second plate is at least 250 um and the sample is deposited on one or both of the plates;
    wherein another of the configurations is a closed configuration, which is the configuration after the sample is deposited in the open configuration; in the closed configuration, at least a part of the sample is inside the microwells, and the average spacing between the inner surface of the first plate and the rim of the microwell in the second plate is less than $\frac{1}{10}$ (one tenth) of the microwell depth.

FIG. 4(b) shows top view of microwells on second plate with (i) round shape with square lattice (ii) rectangle shape with square lattice (iii) triangle shape with hexagonal lattice (iv) round shape with aperiodicity.

Figure 6:
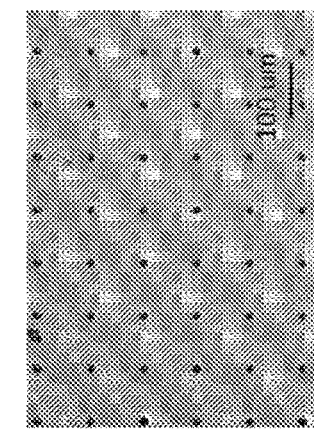
FIG. 6 shows microscopy examples of isolated well array on QMAX first plate fabricated on 0.25 mm thick acrylic substrate, with (a) square well 20 um by 20 um, period 100 um, depth 30 um; (b) square well 20 um by 20 um, period 200 um, depth 30 um; and (c) round well 10 um diameter, period 200 um, depth 20 um.
Figure 6:
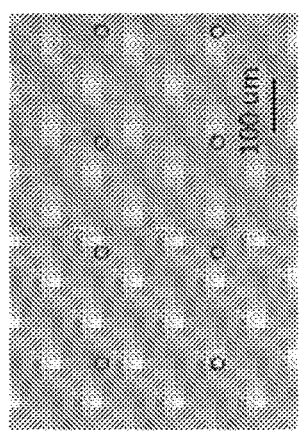
Figure 6:
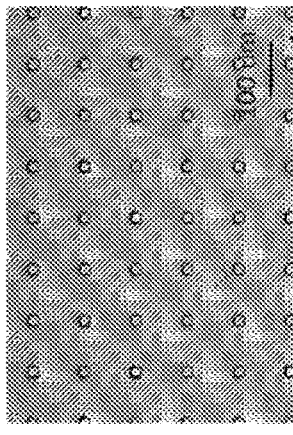

FIG. 6 shows microscopy examples of isolated well array on QMAX first plate fabricated on 0.25 mm thick acrylic substrate, with (a) square well 20 um by 20 um, period 100 um, depth 30 um; (b) square well 20 um by 20 um, period 200 um, depth 30 um; and (c) round well 10 um diameter, period 200 um, depth 20 um.

DD2 A kit for pixelated assaying, comprising:
    a device in embodiment DD1, and
    a imager for imaging the sample contact area.

DD3 A kit for pixelated assaying, comprising:
    a device in embodiment DD1,
    a reagent to be added on to the QMX card with microwells, and
    a imager for imaging the sample contact area.

The kit of any prior embodiment, wherein the reagent is wash solution.

The kit of any prior embodiment, wherein the reagent is a detection agent.

The kit of any prior embodiment, wherein the reagent is an enzyme solution that capable of generating light in a substrate.

M1. A method for pixelated assaying a fluidic sample comprising:
    iii. obtaining a first plate,
    iv. obtaining a second plate,
    wherein
    (a) the first and second plates are movable relative to each other into different configurations, and have, on its respective surface, a sample contact area for contacting a fluidic sample that contains a target analyte;
    (b) the second plate has, in the sample contact area, a plurality of the microwells, wherein each microwell has (i) a well depth of 200 um or less, (ii) a well that ha a volume substantially less than that of the sample, and (iii) a binding site that comprises a capture agent immobilized at the site, and the capture agent is configured to capture the target analyte;

iii. depositing a sample on one or both of the plates; and v. making the plates into a closed configuration;

wherein one of the configurations is an open configuration, in which: the average spacing between the inner surface of the first plate and the rim of the microwells in the second plate is at least 250 um and the sample is deposited on one or both of the plates;

wherein another of the configurations is a closed configuration, which is the configuration after the sample is deposited in the open configuration; in the closed configuration, at least a part of the sample is inside the microwells, and the average spacing between the inner surface of the first plate and the rim of the microwell in the second plate is less than $1/10$ (one tenth) of the microwell depth.

In the method of embodiment M1, wherein the method further comprises, after step (iv), a step of separating the two plates partially or entirely, washing way the original sample or adding an another reagent, and then a step of bring the plates into a closed configuration In the methods of any prior embodiment, wherein the method further comprises a step of imaging the sample contacting area.

In the device or method of any prior paragraph (also referred as "paragraph), wherein the imaging the sample contacting area measures the lump-sum signal related to the analyte from the sample contact area.

In the device or method of any prior paragraph (also referred as "paragraph), wherein the imaging the sample contacting area measures individual signal caused by the individual binding event between a capture agent and the captured target analytes.

In the device or method of any prior paragraph (also referred as "paragraph), wherein the imaging the sample contacting area measures both (a) the lump-sum signal related to the analyte from the sample contact area and (b)individual signal caused by the individual binding event between a capture agent and the captured target analytes.

In the device or method of any prior paragraph (also referred as "paragraph), wherein the existence or concentration of a target analyte in the sample is determined from the detection of the individual signal caused by the individual binding event between a capture agent and the captured target analytes.

In the device or method of any prior paragraph, wherein the volume of each well is configured, for an expected target analyte concentration, so that the distribution of target analyte in each well (that is filled with the sample) follows Poisson distribution.

In the device or method of any prior paragraph, wherein the volume of each well is configured, for an expected target analyte concentration, so that the distribution of target analyte in each well (that is filled with the sample) is, on average, one target analyte per every 2 wells, 3 wells, 5 wells, 10 wells, 20 wells, 0 wells, 50 wells, 75 wells, 100 wells, 150 wells, 200 wells, 300 wells, 500 wells, 1000 wells, 2000 wells, 10000 wells, 100,000 wells, or in a range of any two value.

In the device or method of any prior paragraph, wherein, in the closed configuration, the average spacing between the inner surface of the first plate and the rim of the microwell in the second plate is less than $1/11$ (one eleventh), $1/20$, $1/30$, $1/40$, $1/50$, $1/100$, $1/300$, $1/500$ of the microwell depth, or in a range of any two values.

In the device or method of any prior paragraph, wherein, in the closed configuration, the average spacing between the inner surface of the first plate and the rim of the microwell in the second plate is significantly in contact.

In the device or method of any prior paragraph, wherein, in the closed configuration, the average spacing between two neighboring well is less than 5 nm, 10 nm, 30 nm, 50 nm, 100 nm, 200 nm, 500 nm, 1 um, 2 um, 5 um, 10 um, 20 um, 50 um, 100 um, or in a range of any two values.

The device of prior paragraph, wherein the first plate has well array with shape of sphere, rectangle, hexagon, and/or any other polyhedron, with lattice of square, hexagon, and/or any other lattices.

Fabrication method of the well array on the first plate contains but not limit to nanoimprint lithography, photolithography, interference lithography, e-beam lithography, etc.

In some embodiments, the well on the first plate has periods (average well to well center distance) of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (Period).

In some embodiments, the well on the first plate has well size (average length or diameter) of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (Size).

In some embodiments, the well on the first plate has depth of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (Depth).

In some embodiments, wells have (i) no metal coating (ii) metal coating on bottom of the well (top of the pillar) (iii) metal coating on side wall of the well (side of the pillar) (iv) metal coating on both bottom and side wall of the well.

In some embodiments, the coating metal is gold, aluminum, silver, copper, tin and/or their combinations.

In some embodiments, the well area ratio (ratio of the well area to the total area of the surface) is 40% to 50%, 50% to 60%, 60% to 70%, 70% to 80%, 80% to 90%, 90% to 99%.

In some embodiments, the well edge to well edge distance is larger than the well depth, which is to make sure the diffusion time of well edge to well edge is longer than the diffusion time of well edge to bottom of the well.

In some embodiments, the dimensions of wells are designed to make sure no cross-reaction taking place during the assay process.

In some embodiments, the well numbers on the first plate is much larger than the molecule numbers in the sample, For example, total well number on the first plate is 1 to 2 times, 2 to 5 times, 5 to 10 times, 10 to 100 times, 100 to 1000 times, 1000 to 10000 times of 600, If the molecule concentration is 1 fM with volume of 1 uL;

For example, total well number on the first plate is 1 to 2 times, 2 to 5 times, 5 to 10 times, 10 to 100 times, 100 to 1000 times, 1000 to 10000 times of 600,000, If the molecule concentration is 1 pM with volume of 1 uL;

For example, total well number on the first plate is 1 to 2 times, 2 to 5 times, 5 to 10 times, 10 to 100 times, 100 to 1000 times, 1000 to 10000 times of 600,000,000, If the molecule concentration is 1 nM with volume of 1 uL;

In some embodiments, well number is in such way to achieve, after nucleic acid capture step, most of the wells capture no more than one target molecule.

For example, with well pitch 100 um, total well number on first plate with size of 4 cm$^2$ is 40000. If using such well plate measure 1 fM molecule sample in 1 uL sample, which has 600 target molecule, statistically each well will have no more than one molecule.

In some embodiments, the second plate is an X-Plate.

In some embodiments, the first plate can be any material with flat or engineered solid surface. Examples for the first plate include but are but not limited to: plastic, silicon, PMMA, gold and glass. In some embodiments, the second plate can be any material with flat or engineered solid surface. Examples for the first plate include but are but not limited to: plastic, silicon, PMMA, gold and glass.

In some embodiments, the first plate is made of semiconductors including carbon, germanium, selenium, silicon, gallium arsenide (GaAs), gallium nitride (GaN), indium phosphide (InP), zinc selenide (ZnSe), and silicon carbide (SiC); metals including gold, aluminum, silver, copper, tin and/or their combinations.

As shown in FIG. 4, in some embodiments, the surface of the first plate facing the second plate is defined as the inner surface of the first plate; the surface of the second plate that faces the first plate are also defined as the inner surface of the second plate. In some embodiments, the inner surfaces of the respective plates comprise a sample contact area for contacting a sample that comprises nucleic acid. The sample contact area can occupy part or the entirety of the respective inner surface. As shown in FIG. 4, the second plate can comprises spacers that are fixed on the inner surface of the second plate. It should be noted, however, that in some embodiments the spacers are fixed on the inner surface of the first plate and in other embodiments on the inner surfaces of both the second plate and the first plate.

The sample can be any liquid that needs testing. In some embodiments, the sample is a body fluid that is with or without processing or dilution. For example, the body fluid can be whole blood, blood plasma, serum, urine, saliva, sweat, or breath condensate. In some embodiments, the sample is blood. In certain embodiments, the sample comprises plasma. In certain embodiments, the sample comprises whole blood. In certain embodiments, the sample is a blood or plasma that has been diluted with buffer for 0.5, 1, 2, 3, 4, 5, 6, 7, 8, 9, 10, 20, 30, 40, 50, 60, 70, 80, 90, 100, 200, 300, 400, 500, 600, 700, 800, 900, 1,000, 5,000, 10,000, 50,000, 100,000, 500,000, or 1,000,000 times or in a range between any of the two values. In some embodiments, the sample comprises an analyte, which can be any cell or molecule that can be detected and quantified.

The term "sample" as used herein relates to a material or mixture of materials containing one or more analytes of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The label is a light-emitting label or an optical detectable label, directly or indirectly, either prior to or after it is bound to said capture agent. The label is label with signal of Raman scattering, chromaticity, luminescence, fluorescence, electroluminescence, chemiluminescence, and/or electrochemiluminescence. As used herein, the term "light-emitting label" refers to a label that can emit light when under an external excitation. This can be luminescence. Fluorescent labels (which include dye molecules or quantum dots), and luminescent labels (e.g., electro- or chemiluminescent labels) are types of light-emitting label. The external excitation is light (photons) for fluorescence, electrical current for electroluminescence and chemical reaction for chemiluminscence. An external excitation can be a combination of the above. The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

In some embodiments, there is a signal amplification layer fully or partially on the bottom or side wall or both of the well. The amplification layer amplifies a signal from the target analyte or a label of the target analyte when the target analyte or label is 1 nm, 10 nm, 20 nm, 30 nm, 40 nm, 50 nm, 60 nm, 70 nm, 80 nm, 90 nm, 100 nm, 200 nm, 300 nm, 400 nm, 500 nm, 1 um, 2 um, 5 um, 10 um from the amplification layer, or a range between any two of the values; and a preferred range of 0 nm to 50 nm, 50 nm to 100 nm, 100 nm to 200 nm, 200 nm to 500 nm.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

In some embodiments, the sensing amplification layer includes, but not limited to, the sensing amplification layers described in U.S. Provisional Patent Application No. 61/347,178, which was filed on May 21, 2010, U.S. Provisional Patent Application No. 61/622,226, which was filed on Apr. 10, 2012, U.S. Provisional Patent Application No. 61/708,314, which was filed on Oct. 1, 2012, U.S. Provisional Patent Application No. 61/800,915, which was filed on Mar. 15, 2013, U.S. Provisional Patent Application No. 61/801,933, which was filed on Mar. 15, 2013, U.S. Provisional Patent Application No. 61/801,096, which was filed on Mar. 15, 2013, U.S. Provisional Patent Application No. 61/801,424, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 62/066,777, which was filed on Oct. 21, 2014, U.S. Provisional Patent Application No. 62/234,538, which was filed on Sep. 29, 2015, U.S. Utility patent application Ser. No. 13/699,270, which was filed on Jun. 13, 2013, U.S. Utility patent application Ser. No. 13/838,600, which was filed on Mar. 15, 2013, U.S. Utility patent application Ser. No. 14/459,239, which was filed on Aug. 13, 2014, U.S. Utility patent application Ser. No. 14/459,251, which was filed on Aug. 13, 2014, U.S. Utility patent application Ser. No. 14/852,412, which was filed on Mar. 16, 2014, U.S. Utility patent application Ser. No.

14/871,678, which was filed on Sep. 30, 2015, U.S. Utility patent application Ser. No. 14/431,266, which was filed on Oct. 5, 2015, U.S. Utility patent application Ser. No. 14/668, 750, which was filed on Mar. 25, 2015, U.S. Utility patent application Ser. No. 14/775,634, which was filed on Sep. 11, 2015, U.S. Utility patent application Ser. No. 14/775,638, which was filed on Sep. 11, 2015, U.S. Utility patent application Ser. No. 14/852,417, which was filed on Sep. 11, 2015, U.S. Utility patent application Ser. No. 14/964,394, which was filed on Dec. 9, 2015, PCT Application (desig- nating U.S.) No. PCT/US2011/037455, which was filed on May 20, 2011, PCT Application (designating U.S.) No. PCT/US2013/032347, which was filed on Mar. 15, 2013, PCT Application (designating U.S.) No. PCT/US2013/ 062923, which was filed on Oct. 1, 2013, PCT Application (designating U.S.) No. PCT/US2014/030108, which was filed on Mar. 16, 2014, PCT Application (designating U.S.) No. PCT/US2014/029675, which was filed on Mar. 14, 2014, PCT Application (designating U.S.) No. PCT/ US2014/028417, which was filed on Mar. 14, 2014, PCT Application (designating U.S.) No. PCT/US2014/029979, which was filed on Mar. 15, 2014, PCT Application (des- ignating U.S.) No. PCT/US2015/056518, which was filed on Oct. 20, 2015, PCT Application (designating U.S.) No. PCT/US2016/054025, which was filed on Sep. 27, 2016, the complete disclosures of which are hereby incorporated by reference for all purposes.

The first plate and second plate are moveable relative to each other into different configuration. One of the configu- rations is an open configuration, in which the two plates are partially or entirely separated apart and the spacing between the plates are not regulated by the spacers. FIG. 4 shows the plates in the open configuration, in which a sample, can be added to first plate, the second plate, or both of the plates. In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

Another Example Method of Using the QMAX Device for Pixelated Assay

Figure 5:
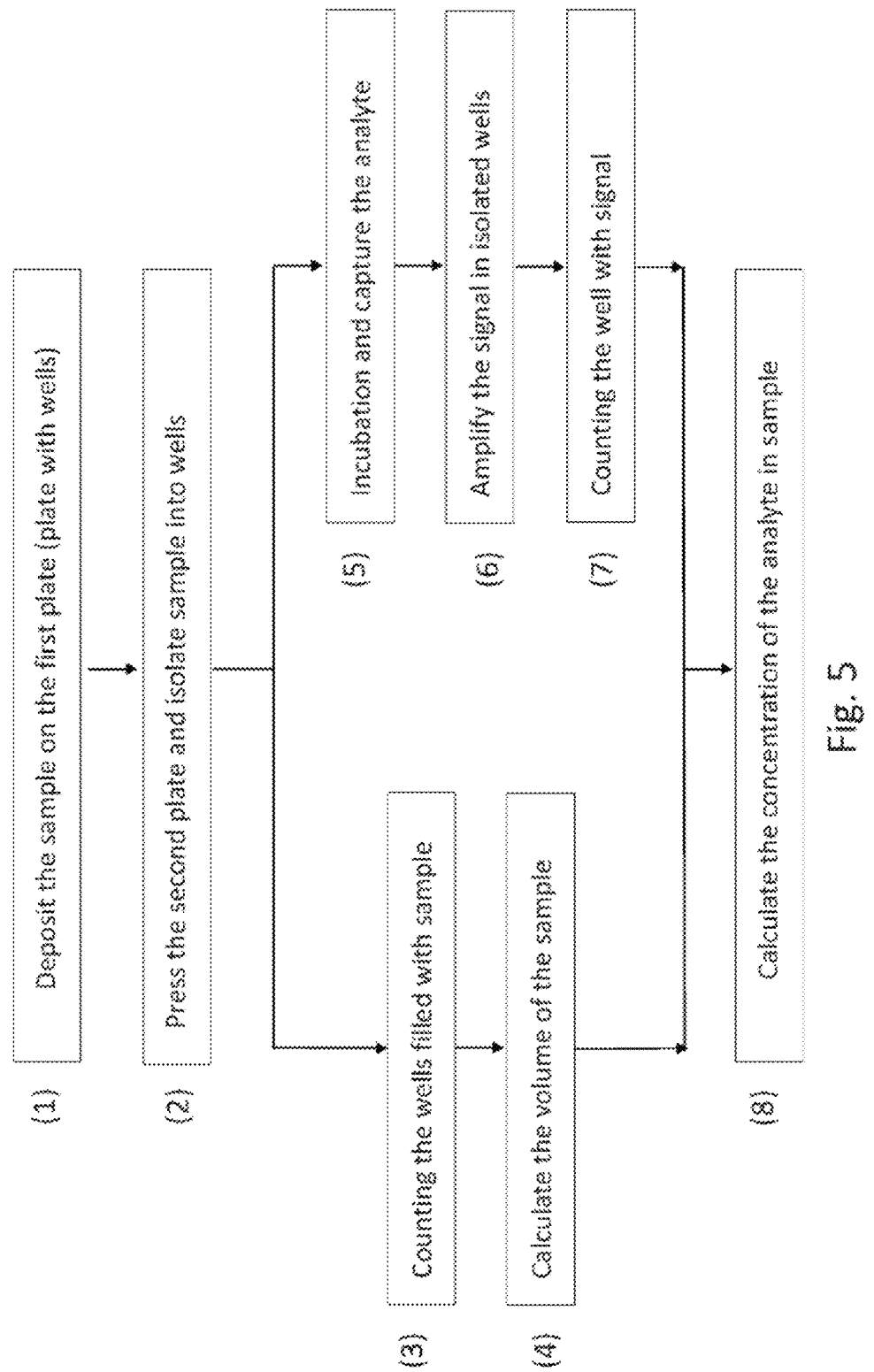
FIG. 5 is an example flow chart showing the basic steps in an exemplary process for conducting a pixelated assay using the QMAX device.

FIG. 5 is an example flow chart showing the basic steps in an exemplary process for conducting a pixelated assay using the QMAX device.

FIG. 5 provides an exemplary flow chart for the process in the "Assay" section. It should be noted, however, the device of the present invention can be used in various assays, including but not limited to measuring the immuno- assay herein described. For example, while FIG. 2 show the process of detecting an analyte using antibodies, it would be possible to use the process and the device that comprises antigens to detect and/or quantify antibodies or antibody expressing cells.

As shown in FIG. 5, in some embodiments, the Pixelated assay process includes: (1) depositing sample at the center of the micro-well plate (first plate shown in FIG. 4); (2) covering with the X-plate (second plate shown in FIG. 1) and pressing the two plate together; (3) counting the wells numbers filled with sample; (4) calculating the volume of the sample by products of well numbers and well volume; (5) incubating and capturing the analyte in isolated wells; (6) amplifying the signal in isolated wells; (7) counting the well with signal; and (8) calculating the concentration of the analyte in sample.

In some embodiments, the method of the present inven- tion, before step (5) and after step (4), further comprise incubating the layer of uniform thickness for a predeter- mined period of time.

In certain embodiments, the predetermined period of time is equal to or longer than the time needed for the target molecule to diffuse into the sample across the layer of uniform thickness.

In certain embodiments, the predetermined period of time is equal to or longer than the time needed for the target molecule to diffuse into the sample across the layer of uniform thickness and captured by capture probe.

In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, for the method of the present invention, the sample is deposited on the first plate. In certain embodiments, before step (5) after step (4), before step (6) after step (5), the sample is incubated on the first plate for a predetermined period of time. In certain embodi- ments, the predetermined period of time is equal to or longer than the time needed for the binding between the capture antibody and the analyte to reach an equilibrium. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, for the method of the present invention, after step (5), and after step (6) the inner surface of the first plate can be washed to remove unbound mol- ecules. For this approach, washing is conducted before switch the plates into the closed configuration. In some embodiments, for the method of the present invention, before step (6) and after step (5), before step (7) and after step (6), the plates can be switched into the open configu- ration (e.g. by removing the second plate) and the inner surface of the first plate can be washed. For this approach, washing is conducted before switch the plates into the closed configuration. In certain embodiments, such a step reduces non-specific binding and reduce signal noise. In certain embodiments, each of the wash step includes only one or multiple washes. In some embodiments, both of the washing steps are conducted. In some embodiments, only one of the washing steps is conducted.

In some embodiments, the inner surface can be washed with washing solution absorbed in a sponge. In some embodiments, the washing is conducted by squeezing the sponge to release the wash solution onto the inner surface of the first plate and releasing the sponge to reabsorb the wash solution. In some embodiments, the washing improves the limit of detection (LOD) for the detectable signal.

The amplification method in (6) amplification step includ- ing, but not limit to:

The color based enzymatic reaction, the absorption signal generated by substrates are amplified by enzyme which are linked to the detection reagents; wherein the enzyme includ- ing horseradish peroxidase; wherein the substrates including ABTS or TMB;

The fluorescence based enzymatic reaction, the fluores- cence signal generated by substrates are amplified by enzyme which are linked to the detection reagents; wherein the enzyme including horseradish peroxidase; wherein the substrates including Amplex red;

Catalytic amplification. An analyte activates a catalyst, which then produces multiple copies of a reporter molecule.

Catalytic self-amplification. An analyte activates a catalyst, which results in the production of reporter molecules. These not only generate a signal, but are also able to activate the catalyst. Analyte-induced modification of a collective property. The binding of a single analyte molecule to a receptor affects the properties of neighboring units through signal transduction.

Multivalent surfaces for binding of multiple analyte molecules. Recruitment of multiple reporters using multivalent scaffolds such as polymers, dendrimers or nanoparticles amplifies the signal.

Wherein above catalysts including Pd(0)-catalyst, apyrase, potassium permanganate, platinum, etc.

In certain embodiments, amplification substrates are added before step (6), the amplification substrates includes but limited to ABTS and TMB.

In certain embodiments, before step (7) after step (6), the sample is incubated on the first plate for a predetermined period of time. In certain embodiments, the predetermined period of time is equal to or longer than the time needed for the amplification process. In certain embodiments, the predetermined period of time is equal to or longer than the time needed for the well have readable signal. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In step (3) counting the wells numbers filled with sample; and (7) counting the well with signal, various types of "detection methods" including but not limited to using fluorescence microscopy, DSLR (Digital single-lens reflex camera) and smart-phone.

In step (4) calculating the volume of the sample, all the wells are observed and counted, or partial of the wells are observed and counted. The total volume of sample in QMAX is estimated from the product of counting number and well volume.

With the fact that well number is much larger than the total molecule number in sample, statistically each well has no more than one molecule. The total molecule number in the sample is estimated by count the wells number with signal after the amplification step. The final concentration of analyte in sample is calculated by divide the molecule number over sample volume.

Other Examples of Present Invention

FIG. 4 shows schematics of preparation of binding site plate (first plate) and storage plate (second plate) of an exemplary embodiment for pixelated assay QMAX. The experiment process follows the flow chart of FIG. 5.

Specifically, the first plate in this example is square well array with size of 20 um by 20 um, period of 100 um, depth of 30 um fabricated on 0.25 mm thick acrylic substrate. Protein-A 10 ug/mL in PBS coat the first plate for 2 hours, followed by washing three times with PBST. The first plate was then coated with anti-human IgG capture antibody (goat anti-human IgG) 10 ug/mL in PBS coat for 2 h, followed by blocking with 4% BSA in PBS for 2 hours. The first plate was then incubated with 100 ul STABILCOAT® protein stabilizer for 2 hours. Excessive liquid was removed and the plate was dried at room temperature.

The second plate in this example is a flat 0.175 mm thick acrylic film. Detection Ab (mouse anti-human IgG) conjugated HRP 10 ug/mL 200 uL uniformly printed and dried on it at 37° C. for 2 hours.

Figure 7:
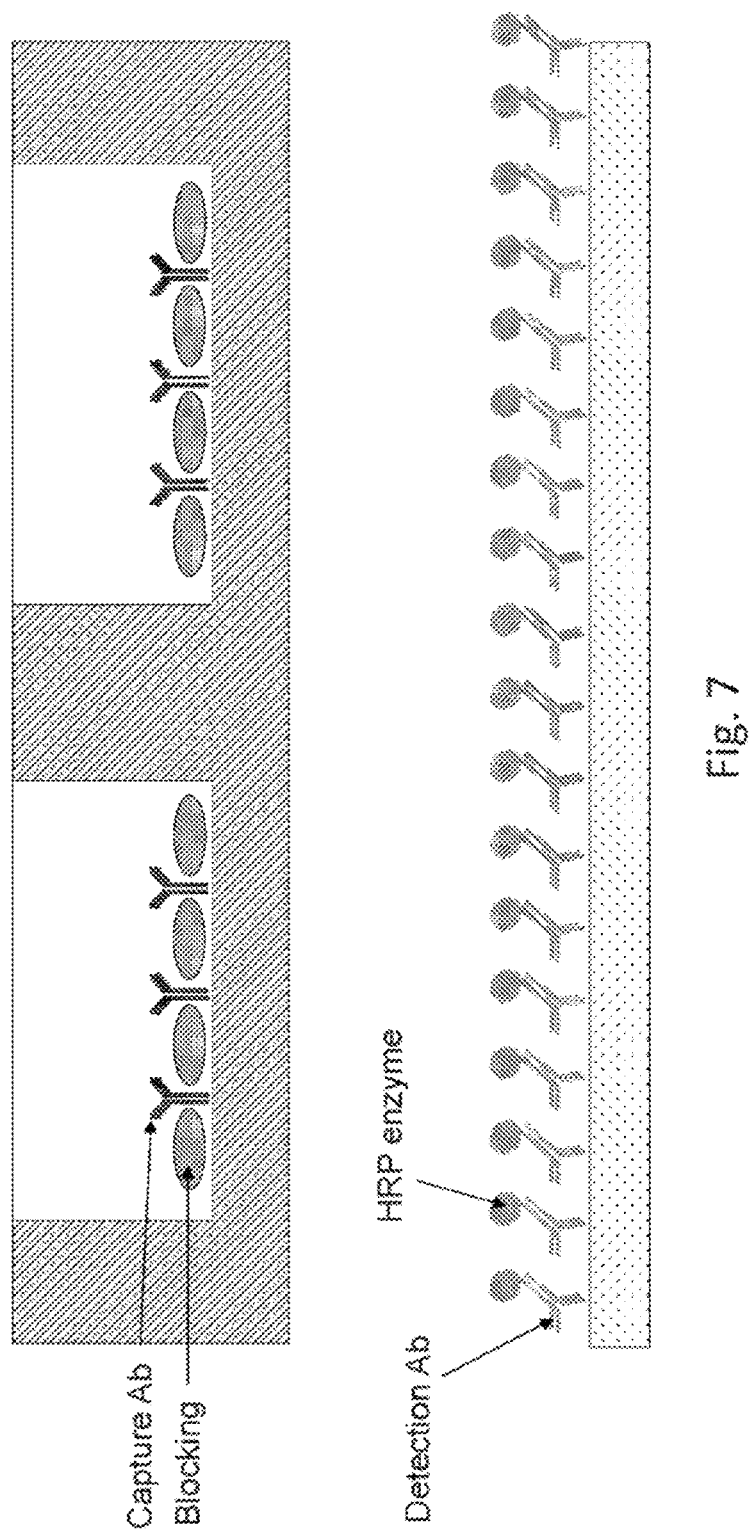
FIG. 7 shows schematics of preparation of binding site plate (first plate) and storage plate (second plate) of an exemplary embodiment for performing pixelated assay QMAX.

As shown in FIG. 7, in some embodiments the first plate comprises a capture antibody that is fully or partially coated on the inner surface of the first plate. In some embodiments the capture antibody is fully or partially on the bottom or side wall or both of the well on the first plate.

In some embodiments, the capture antibody can be applied to the surface by printing, spraying, soaking or any other method that applies homogenous or partial layer of reagents. In certain embodiments, the capture antibody is dried on the first plate. It should also be noted that in some embodiments the capture antibody is coated on the inner surface of the first plate, not the second plate; in some embodiments the capture antibody is coated on the inner surface of the second plate, not the first plate; in some embodiments the capture antibody is coated on the inner surfaces of both plates. In some embodiments, the capture antibody is either monocolonal, polycolonal antibody, engineered antibody (e.g. single chain variable fragments (scFv)) or fragments thereof. In some embodiments, the concentration of coated capture antibody ranges from 1 fg/mL to 1 g/mL.

In some embodiments, the capture antibody is configured to bind to the analyte. For example, when the analyte comprises an antigen epitope, in certain embodiments the capture antibody is configured to specifically bind to the antigen epitope. In some embodiments, the capture antibody is (a) covalently bound to the surface, or (b) attached to the surface by passive absorption through hydrophobic interactions between solid surface and non-polar residues on the proteins. For example, in some embodiments as shown in FIG. 4, the capture antibody is attached to the first plate 10 through protein A. In certain embodiments, the capture antibody can immobilize the analyte 95 onto the inner surface of the first plate.

While antibodies can be used to detect antigens, antigens can also be used to detect antibodies. For example, in some embodiments the present invention, a capture antigen (or epitope), instead of the capture antibody, can be coated on the inner surface of a respective plate (e.g. the first plate). The capture antigen can be attached to the inner surface and used to immobilize an analyte (e.g. antibody or antibody-expressing cell) onto the inner surface.

As shown in FIG. 7, in some embodiments the first plate comprises blockers that are coated on the inner surface of the first plate. In some embodiments, the blockers block any unoccupied sites on the solid surface that can cause unwanted nonspecific bindings in assays. In certain embodiments, the blocker reduces nonspecific binding. In certain embodiments, the blockers can be applied to the surface by printing, spraying, soaking or any other method that applies homogenous layer of reagents. In certain embodiments, the blockers are dried on the first plate. It should also be noted that in some embodiments the blockers are coated on the inner surface of the first plate, not the second plate; in some embodiments the blockers are coated on the inner surface of the second plate, not the first plate; in some embodiments the blockers are coated on the inner surfaces of both plate. In some embodiments, the blockers are bovine serum albumin (BSA), casein or total proteins from whole milk, etc.

As shown in FIG. 7, in some embodiments the first plate comprises a stabilizer that is coated on the inner surface of the first plate. In some embodiments, the stabilizer helps maintain the proper folding of protein when dried so that the function of the protein is not disrupted during storage. In certain embodiments, the stabilizer prolongs the usage life span of the reagents, such as but not limited to a protein. In certain embodiments, the stabilizer can be applied to the surface by printing, spraying, soaking or any other method that applies homogenous layer of reagents. In certain embodiments, the stabilizer is dried on the first plate. It should also be noted that in some embodiments the stabilizer is coated on the inner surface of the first plate, not the second plate; in some embodiments the stabilizer is coated on the inner surface of the second plate, not the first plate; in some embodiments the stabilizer is coated on the inner surfaces of both plates. In some embodiments, the stabilizer is sugar such as but not limited to sucrose and glucose. In some embodiments, the stabilizer is a polymer. In certain embodiments, the stabilizer is glycerol.

As shown in FIG. 7, in some embodiments the second plate comprises a detection antibody that is coated on the inner surface of the second plate. In some embodiments, the detection antibody can be applied to the surface by printing, spraying, soaking or any other method that applies homogenous layer of reagents. In certain embodiments, the detection antibody is dried on the second plate. It should also be noted that in some embodiments the detection antibody is coated on the inner surface of the second plate, not the first plate; in some embodiments the detection antibody is coated on the inner surface of the first plate, not the second plate; in some embodiments the detection antibody is coated on the inner surfaces of both plates. In some embodiments, the detection antibody is either monoclonal, polyclonal antibody, engineered antibody (e.g. single chain variable fragments (scFv)) or fragments thereof. In some embodiments, the concentration of coated detection antibody ranges from 1 fg/mL to 1 g/mL.

In some embodiments, the detection antibody is configured to bind to the analyte. For example, when the analyte comprises an antigen epitope, in certain embodiments the detection antibody is configured to specifically bind to the antigen epitope. In certain embodiments, the capture antibody and the detection antibody bind to different sites (e.g. epitopes) of the analyte. In certain embodiments, the detection antibody is configured to specifically bind to a capture antibody-analyte complex. In certain embodiments, the detection antibody is not covalently bound to the inner surface. In certain embodiments, the detection antibody is not attached to the surface by passive absorption through hydrophobic interactions between solid surface and nonpolar residues on the proteins. In certain embodiments, the detection antibody 160 can diffuse into the sample after the sample is deposited and the detection antibody is in contact with the sample liquid.

In some embodiments, the detection antibody is configured to produce a detectable signal after binding to the analyte. For example, in some embodiments the signal can be a colorimetric signal, a luminescent signal, or a fluorescent signal. In some embodiments for example, the detection antibody is labeled by a fluorescent label 165, which produces a signal after the detection antibody 1 binds to the analyte or to the capture antibody-analyte complex. In some embodiments, the fluorescent label directly labels the detection antibody. In some embodiments, the fluorescent label 165 labels a reagent that can bind to the detection antibody 160 or a detection antibody-analyte complex. In some embodiments, the secondary antibody can be conjugated with an optical detectable label, e.g., a fluorophore such as but not limited to cy5, IR800, SAPE IRDye800CW, Alexa 790, Dylight 800. In some embodiments, the labels on the capture antibody, or detection antibody, or the analyte are nucleic acids. The presence and concentration of the nucleic acids is quantified by real-time PCR amplification.

In some embodiments, the detection antibody is configured to a chemical that can amplified signal or the signal from this chemical can be amplified; wherein amplification method in this amplification step including, but not limit to:

The color based enzymatic reaction, the absorption signal generated by substrates are amplified by enzyme which are linked to the detection reagents; wherein the enzyme including horseradish peroxidase; wherein the substrates including ABTS or TMB;

The fluorescence based enzymatic reaction, the fluorescence signal generated by substrates are amplified by enzyme which are linked to the detection reagents; wherein the enzyme including horseradish peroxidase; wherein the substrates including Amplex red;

Catalytic amplification. An analyte activates a catalyst, which then produces multiple copies of a reporter molecule.

Catalytic self-amplification. An analyte activates a catalyst, which results in the production of reporter molecules. These not only generate a signal, but are also able to activate the catalyst.

Analyte-induced modification of a collective property. The binding of a single analyte molecule to a receptor affects the properties of neighboring units through signal transduction.

Multivalent surfaces for binding of multiple analyte molecules. Recruitment of multiple reporters using multivalent scaffolds such as polymers, dendrimers or nanoparticles amplifies the signal.

Wherein above catalysts including Pd(0)-catalyst, apyrase, potassium permanganate, platinum, etc.

While antibodies can be used to detect antigens, antigens can also be used to detect antibodies. For example, in some embodiments of the present invention, a detection antigen (or epitope), instead of the detection antibody, can be coated on the inner surface of a respective plate (e.g. the second plate). The capture antigen can be attached to the inner surface and used to detect an analyte (e.g. antibody or antibody-expressing cell) onto the inner surface.

As shown in FIG. 7, in some embodiments the second plate comprises stabilizers, which stabilizes the proteins (e.g. the detection antibody) and prolongs the shelf-life of the device. In some embodiments, the stabilizer helps maintain the proper folding of protein when dried so that the function of the protein is not disrupted during storage. In certain embodiments, the stabilizer prolongs the usage life span of the reagents, such as but not limited to a protein. In certain embodiments, the stabilizer can be applied to the surface by printing, spraying, soaking or any other method that applies homogenous layer of reagents. In certain embodiments, the stabilizer is dried on the first plate. It should also be noted that in some embodiments the stabilizer 155 is coated on the inner surface of the first plate, not the second plate; in some embodiments the stabilizer is coated on the inner surface of the second plate, not the first plate; in some embodiments the stabilizer is coated on the inner surfaces of both plates. In some embodiments, the stabilizer is sugar such as but not limited to sucrose and glucose. In some embodiments, the stabilizer is a polymer. In certain embodiments, the stabilizer is glycerol. In some embodiments, the stabilizer coated on the first plate and the stabilizer coated on the second plate are the same. In some embodiments, the stabilizer coated on the first plate and the stabilizer coated on the second plate are different.

Figure 8:
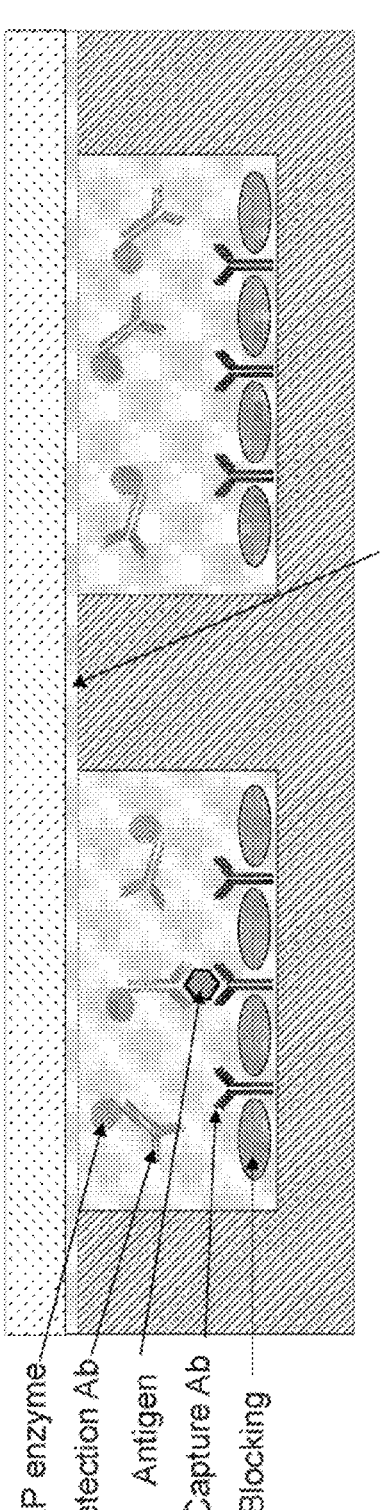
FIG. 8 shows a schematic drawing for an exemplary embodiment of a pixelated assay QMAX device in a closed configuration for incubation process.

FIG. 8 shows a schematic drawing for an exemplary embodiment of a pixelated assay QMAX device in a closed configuration for capturing process. In this process, 1) Drop 1 uL antigen (human IgG in PBS) with concentrations of 1 ng/mL to 1 fg/mL on first plate
2) Press the second plate on top of the liquid by hand.
3) Take the photo of wells on first plate. The volume of total sample is calculated by counting the well filled with sample.
4) Incubate for 1 min.
5) Peel off the second plate/Wash the first plate inside PBST for 1 min, then water for 1 min.

Figure 9:
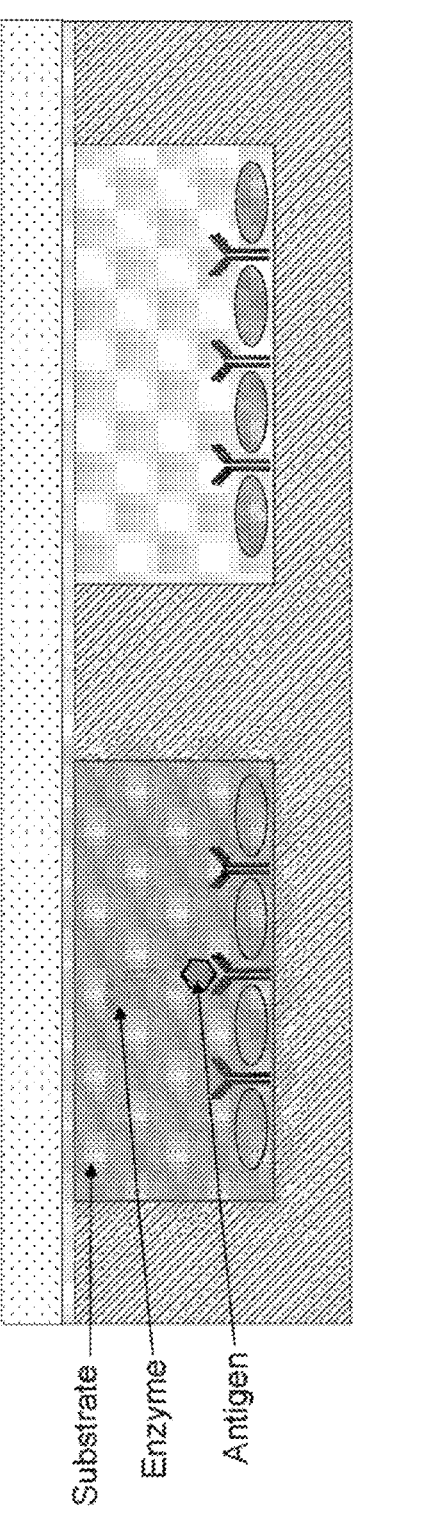
FIG. 9 shows a schematic drawing for an exemplary embodiment of a pixelated assay QMAX device in a closed configuration for amplification process.

FIG. 9 shows a schematic drawing for an exemplary embodiment of a pixelated assay QMAX device in a closed configuration for amplification process. In this process, 5) Drop 3 uL (over amount) TMB amplification substrate on first plate;
6) Press the amplification second plate on top of the liquid by hand;
7) Incubate for 1 min. In this process, only the well captured antigen get amplified and show signal (color or fluorescence);
8) Peel off the amplification second plate/Wash the first plate inside PBST for 1 min, then water for 1 min.

Further Examples for QMAX Pixelated Assay Results

Figure 10:
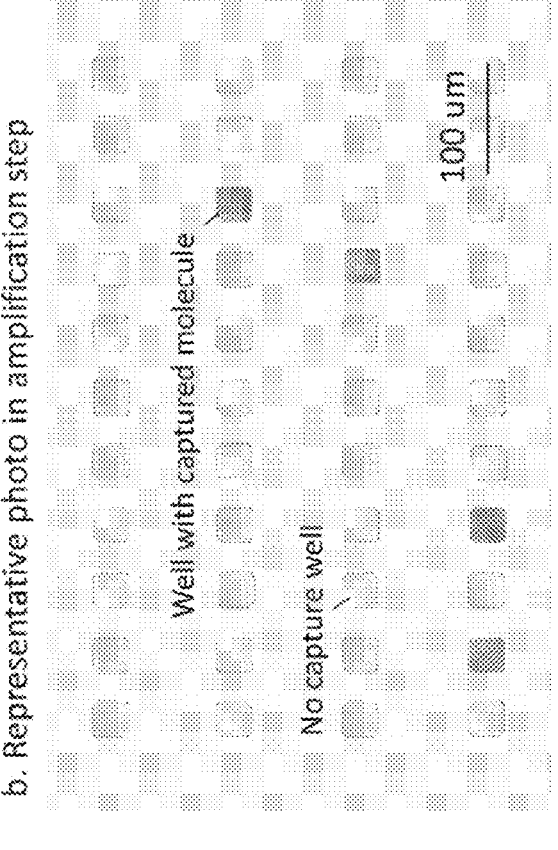
FIG. 10 shows representative measurement figure of pixelated assay with isolated well. (a) The sample volume is estimated by counting the well filled with sample in the capture step. (b) The molecule number in the sample is estimated by count the wells number with signal after the amplification step. The final concentration of analyte in sample is back calculated by dividing the molecule number over sample volume.
Figure 10:
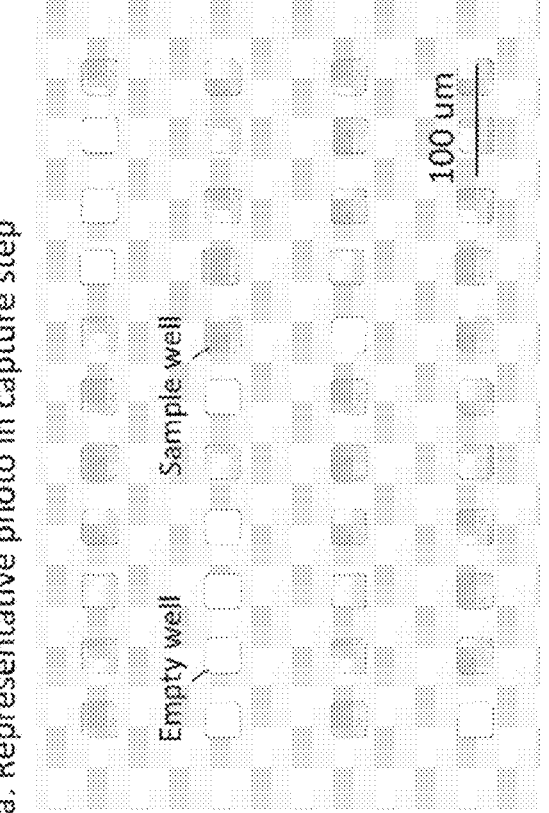

FIG. 10 representative measurement figure of pixelated assay with isolated well. (a) The sample volume is estimated by counting the well filled with sample in the capture step. (b) The molecule number in the sample is estimated by count the wells number with signal in the amplification step. The final concentration of analyte in sample is the molecule number over sample volume.

Consider statistically each well has no more than one molecule, by counting the well numbers with amplified signal, the QMAX pixelated assay has molecule level sensitivity.

As demonstrated by the examples, in some embodiments, the present invention provides a platform for assay, that is fast, simple, portable and only requires as little as 1 µL or less of sample, have sensitivity to molecule level concentration. With the current invention, assay can be performed in a shallow enclosed space with designated parameters so that the sample volume and capturing time can be accurately controlled. In some embodiments, Brownian motion of molecules is restricted in the shallow space so that equilibrium of molecule binding can be reached faster. This platform can be adapted for any assay that are performed in traditional micro titter plate and thus have broad applications.

Examples of Pixelated Detection of Analyte with Homogenous Assay

In the device or method of any prior embodiments, the well generates the signal when the analyte in the sample contacts and reacts the chemicals and reagents stored in the well. No any washing step is conducted in the process.

In some embodiments the signal can be a colorimetric signal, a luminescent signal, a fluorescent signal, an absorptance signal or micro/nano pattern change.

In some embodiments, the signal is generated with one chemical reaction. For example, horseradish peroxidase directly reacts with 3,5,3',5'-tetramethylbenzidine (TMB).

In some embodiments, the signal is generated with a chain chemical reaction. For example, alcohol react with alcohol oxidase to generate hydrogen peroxide, then hydrogen peroxide reacts with horseradish peroxidase and amplex red.

In some embodiments, after the signal is generated, the signal is further amplified homogenously. For example, initial signal is generated by nucleic acid. A following polymerase chain reaction (PCR) is performed to generate and amplify the signal in each well.

In some embodiments, the homogenous pixelated assay process includes: (1) depositing sample at the center of the micro-well plate (first plate shown in FIG. 4); (2) covering with the X-plate (second plate shown in FIG. 1) and pressing the two plate together; (3) counting the wells numbers filled with sample; (4) calculating the volume of the sample by products of well numbers and well volume; (5) incubating the analyte in isolated wells, and generating the signal in isolated wells; (7) counting the well with signal; and (8) back-calculating the concentration of the analyte in sample.

In some embodiments, the reagents are dried and uniformly coated on the bottom of the microwells.

In some embodiments, the reagents are in liquid form and are sealed with a thin film on the bottom of the microwells.

In some embodiments, the reagents are dried and uniformly coated on the side walls of the microwells.

In some embodiments, the reagents are dried and uniformly coated on other plate without microwells.

Some of the colorimetric assay examples use in the system are given as following:

1. Glucose Colorimetric (Fluorimetric) assay with Glucose Oxidase 100 unit/ml, Horseradish Peroxidase 100 unit/ml, 4-amino antipyrine 20 mM, and TOOS 20 mM, 3,5,3',5'-Tetramethylbenzidine (TMB) 20 mM, Amplex Red 20 mM, Hexokinase 1 unit/ml, ATP220 g/ml, NAD 400 g/ml.
2. Calcium Colorimetric assay with Arsenazo III 17 ug/ml.
3. Albumin Colorimetric assay with Bromcresol purple 22 ug/ml.
4. Total Protein Colorimetric assay with Cupric sulfate 1.34 mg/ml, Sodium potassium tartrate 3.43 mg/ml, Potassium iodide 0.28 mg/ml.
5. Sodium Colorimetric assay with ONPG 220 ug/ml, β-Galactosidase 0.05 unit/ml.
6. Potassium Colorimetric assay with ADP 220 ug/ml, Phosphoenolpyruvate 0.05 unit/ml, Pyruvate kinase 0.1 unit/ml, NADH 480 ug/ml, Potassium phosphateb 13.6 mg/ml, Magnesium sulfate 95 ug/ml, FAD 7.85 ug/ml, 4-Aminoantipyrine 130 ug/ml, Horseradish Peroxidase 10 unit/ml and TBHBA 1.88 mg/ml.
7. Chloride Colorimetric assay with CNPG3 530 ug/ml, Amylase 0.36 unit/ml, Calcium acetate 250 ug/ml.
8. Blood Urea Nitrogen Colorimetric assay with Urea Amidolyase, PEP, ATP, Pyruvate Kinase, Pyruvate Oxidase, Potassium phosphate, MgCl2, FAD, TBHBA, 4-AAP, Peroxidase.
9. Creatinine Colorimetric assay with Creatinine Amidohydrolase, Creatinine Amidinohydrolase, Sarcoosine Oxidasem, TBHBA, 4-AAP, Peroxidase.
10. Alkaline Phosphatase Colorimetric assay with p-Nitrophenyl Phosphate, Zinc Sulfate, Magnesium Sulfate.
11. Alanine Amino Transferase Colorimetric assay with L-Alanine, α-Ketoglutaric Acid, Pyruvate Oxidase, Potassium phosphate, MgCl2, FAD, TBHBA, 4-AAP, Peroxidase.
12. Hydrogen Peroxide (Fluorimetric) assay with Horseradish Peroxidase, 4-amino antipyrine, TOOS, 3,5,3', 5'-Tetramethylbenzidine (TMB), Amplex Red.
13. Amylase (Colorimetric) assay with Starch, Sodium Chloride, Sodium hydroxide, Sodium potassium tartrate, 3,5 DNS (Dinitro Salicylic acid).
14. Lactate (Colorimetric) assay with Lactate dehydrogenase, NAD+, Diaphorase, INT (Iodonitrotetrazolium).

15. Lactate dehydrogenase (Colorimetric) assay with Sodium L-Lactate, NAD+, Diaphorase, INT (Iodonitrotetrazolium).

16. Glutamine (Colorimetric) assay with Glutamine dehydrogenase, NAD+, Diaphorase, INT (Iodonitrotetrazolium).

Additional Examples

1. A device for assaying a fluidic sample comprising:

a first plate, a second plate, and microwells, wherein (a) the first and second plates are movable relative to each other into different configurations, and have, on its respective surface, a sample contact area for contacting a fluidic sample that contains a target analyte;

(b) the second plate has, in the sample contact area, a plurality of the microwells, wherein each microwell has (i) a well depth of 200 um or less, (ii) a well volume substantially less than that of the sample, and (iii) a binding site with capture agents immobilized at the site, and the capture agent is configured to capture the target analyte;

wherein one of the configurations is an open configuration, in which: the average spacing between the inner surface of the first plate and the rim of the microwells in the second plate is at least 250 um and the sample is deposited on one or both of the plates;

wherein another of the configurations is a close configuration, which is the configuration after the sample is deposited in the open configuration; in the closed configuration, at least a part of the sample is inside the microwells, and the average spacing between the inner surface of the first plate and the rim of the microwell in the second plate is less than $\frac{1}{10}$ (one tenth) of the microwell depth.

2. A kit for analyzing a sample comprising:

(a) a device of embodiment 1;

(b) a sponge that is configured to release a solution stored in the sponge to outside and absorb a solution outside the sponge to inside the sponge.

3. A system for analyzing a sample comprising:

(a) a device of claim 1;

(b) a reading device for producing an image of signals emanating from the binding site of the second plate;

(c) a device assembly that operably connects the reading device to the closed configuration of the first plate and second plate;

(d) a memory for storing said image; and (e) programming for identifying and counting individual binding events in an area of the image.

4. A method of assaying a fluidic sample, comprising:

(a) obtaining a sample that contains a target analyte;

(b) obtaining a device of embodiment 1;

(c) depositing the sample on one or both of the plates when the plates are configured in the open configuration;

(d) after (c), moving the two plates of the device of embodiment 1 into the close configuration,; and (e) reading the sample contact area of the second plate with a reading device to produce an image of signals.

2-1. The kit of embodiment 2, wherein the kit further comprises a detection agent.

2-2. The kit of embodiment 2, wherein the kit further comprises a detection agent and a substrate, and the detection agent and substrate are configured to together generate a product that either emitting light or creates a color.

2-2.1. The kit of embodiment 2-2, wherein the detection agent is an enzyme which are linked to the detection reagents as horseradish peroxidase, the substrate is color based as ABTS or TMB;

2-2.2. The kit of embodiment 2-2, wherein the detection agent is an enzyme which are linked to the detection reagents as horseradish peroxidase, the substrate is fluorescence based as amplex red;

2-3. The kit of embodiment 2, wherein the kit further comprises units, which the binding of a single analyte molecule to a receptor affects the properties of neighboring units through signal transduction. (Analyte-induced modification of a collective property).

2-4. The kit of embodiment 2, wherein the kit further comprises one or more catalysts, and the catalysts include Pd(0)-catalyst, apyrase, potassium permanganate, or platinum, etc.

3-1. The system of embodiment 3, wherein the device assembly is an adaptor that connects to a camera of a handheld mobile communication device.

3-2. The system of embodiment 3, wherein the signals represent individual target-analyte binding events.

3-3. The system of embodiment 3, wherein the device assembly controls or changes the relative position between the plate and the reading device, in at least one of the three (x, y, z) orthogonal directions, for reading the signals.

3-4. The system of embodiment 3, wherein the reading device is a CCD camera.

3-5. The system of embodiment 3, wherein the reading device is a photodetector comprising one or more other optical devices that are selected from optical filters, spectrometer, lenses, apertures, beam splitter, mirrors, polarizers, waveplates, and shutters.

3-6. The system of embodiment 3, wherein the reading device collects the position, local intensity, local spectrum and local Raman signature of said signals.

3-7. The system of embodiment 3, wherein the programming comprises programming for: (1) determining the local intensity or spectrum or Raman signature of background signal, (2) determining local signal intensity or spectrum or Raman signature for one label, two labels, three labels, and four or more labels; and (3) determining the total number of labels in the imaged area.

3-8. The system of embodiment 3, wherein the identifying and counting comprises determining of any, some, or all of the local intensity, spectrum, and Raman signatures.

3-9. The system of embodiment 3, further comprising a source of light, electricity, or chemical for exciting labels on the surface of said plate.

3-10. The system of embodiment 3 wherein said system comprises an electrode for applying a voltage between the electrode and the sensing amplification layer for generating an electric field and/or electrical field gradient that either (a) moves analytes that have been placed in solution on the surface of the plate to the capture agents on the sensing amplification layer.

3-11. The system of embodiment 3, wherein said system comprises an electrode for applying a voltage bias between said signal amplification layer and another electrode to further improve sensitivity.

3-12. The system of embodiment 3, wherein the reading device is an electric or mechanical or biological probe that collects the position, local electrical, local mechanical, local biological, and local optical interaction between the plate and the reading device.

3-13. The system of embodiment 13, wherein the reading device is a camera of a handheld mobile communication device.

4-1. The method of embodiment 4, wherein the method further comprises a step of washing to remove any biological materials that are not bound to the capture agent.

4-1. The method of embodiment 4, wherein the method does not comprise any steps of washing to remove any biological materials that are not bound to the capture agent.

4-2. The method of embodiment 4, wherein the method further comprises a step of adding a detection agent.

4-3. The method of embodiment 4, wherein the method further comprises steps of (i) adding a detection agent, (ii) washing to remove any unbound detection agent, and (iii) adding a substrate to generate color.

4-4. The method of embodiment 4, wherein the reading in the step (e) is performed with the plates in the closed configuration and the microwells has substrate.

4-5. The method of embodiment 5, wherein the method is a homogeneous assay that the signal is read without using a wash step to remove any biological materials or labels that are not bound to the capture agent at the binding site.

5. The device, kit, system, or method of any prior embodiments, wherein the binding area has a signal amplification layer and the capture agents are immobilized on the signal amplification layer.

6. The device, kit, system, or method of prior embodiments, wherein microwell period is 1 nm to 10 nm, 10 nm to 100 nm, 100 nm to 500 nm, 500 nm to 1 um, 1 um to 5 um, 5 um to 50 um, 50 um to 500 um, 500 um to 1 mm, or 1 mm to 5 mm; with preferred ranges of 1 um to 10 um, 10 um to 50 um, or 50 um to 500 um.

7. The device, kit, system, or method of any prior embodiments, wherein microwell size (length or diameter) is 1 nm to 10 nm, 10 nm to 100 nm, 100 nm to 500 nm, 500 nm to 1 um, 1 um to 5 um, 5 um to 50 um, 50 um to 500 um, 500 um to 1 mm, or 1 mm to 5 mm; with preferred ranges of 0.5 um to 5 um, 5 um to 25 um, or 25 um to 300 um.

8. The device, kit, system, or method of any prior embodiments, wherein microwell depth is 1 nm to 10 nm, 10 nm to 100 nm, 100 nm to 500 nm, 500 nm to 1 um, 1 um to 5 um, 5 um to 50 um, 50 um to 500 um, 500 um to 1 mm, or 1 mm to 5 mm; with preferred ranges of preferred 0.5 um to 5 um, 5 um to 25 um, or 25 um to 300 um;

9. The device, kit, system, or method of any prior embodiments, wherein the microwells have shapes of sphere, rectangle, hexagon, and/or any other polyhedron.

10. The device, kit, system, or method of prior embodiments, wherein the microwells are periodic with lattice of square, hexagon, and/or any other lattices.

11. The device, kit, system, or method of any prior embodiments, wherein the microwells are aperiodic with average period in above embodiment 6.

12. The device, kit, system, or method of any prior embodiments, wherein the microwell area ratio (ratio of the microwell area to the total area of the surface) is at least 40%, 50%, 60%, 70%, 80%, 90%, 95%, or 99%, or in a range between any of the two values.

13. The device, kit, system, or method of any prior embodiments, wherein the material of the plates is polystyrene, PMMA, PC, COC, COP, or another plastic.

14. The device, kit, system, or method of any prior embodiments, wherein the microwell distance (period minus size) is larger than the microwell depth; being configured to ensure diffusion time of analyte from one microwell to other is longer than the incubation time (the diffusion time of the microwell depth).

15. The device, kit, system, or method of any prior embodiments, wherein one or both of the plates comprise spacers that are permanently fixed on the inner surface of a respective plate.

15-1. The device, kit, system, or method of embodiment 15, wherein the spacers have a predetermined substantially uniform height that is equal to or less than 200 microns, and a predetermined inter-spacer-distance;

16. The device, kit, system, or method of any prior embodiments, wherein the average spacing between the plates in the closed configuration is 100 um or less.

17. The device, kit, system, or method of any prior embodiments, wherein the average spacing between the plates in the closed configuration is 50 um or less.

15. The device, kit, system, or method of any prior embodiments, wherein the device further comprises a hinge that connects the first plate and the second plate, and is configured to allow the plates to rotate around the hinge into different configurations.

19. The device, kit, system, or method of any prior embodiments, wherein at least one of the plates is flexible 20. A method of assaying a fluidic sample, comprising:
   (a) obtaining a sample that contains a target analyte;
   (b) obtaining a device of embodiment 1;
   (c) depositing the sample on one or both of the plates when the plates are configured in the open configuration;
   (d) after (c), moving the two plates of the device of embodiment 1 into the closed configuration; and
   (e) reading the sample contact area of the second plate with a reading device to produce an image of signals.

20-1. The method of embodiment 20, further comprising:
   (f) quantifying a signal in an area of the image to providing an estimate of the amount of one or more analytes in the sample.

20-2. The method of embodiment 20-1, wherein step (f) comprises identifying and counting individual binding events between an analyte with a capture agents in an area of the image, thereby providing an estimate of the amount of one or more analytes in the sample.

20-3. The method of embodiment 20-1, wherein step (f) comprises quantifying a lump-sum signal in an area of the image, thereby providing an estimate of the amount of one or more analytes in the sample.

20-4. The method of embodiment 20, wherein the sample contact area of the second plate has a reagent storage site.

20-5. The method of embodiment 20, wherein the sample contact area of the second plate has a reagent storage site, and the storage site is, in a closed configuration, approximately above the binding site on the first plate.

20-6. The method of embodiment 20, wherein the sample contact area in the first plate further comprises a reagent storage site.

20-7. The method of embodiment 20, wherein the sample contact area in the first plate further comprises a reagent storage site, wherein the reagent storage site is not in the same location of the sample contact area as that of the binding site.

20-8. The method of embodiment 20-7 wherein the reagent in the reagent storage site is a detection agent that binds to the target analyte.

20-9. The method of embodiment 20, wherein the method further comprises a step of labeling the target analyte with a detection agent.

20-10. The method of embodiment 20-9, wherein the detection agent comprises a label.

20-11. The method of embodiment 20-9, wherein the capture agent and detection agent both bind to the target analyte to form a sandwich.

20-12. The method of embodiment 20, wherein the method further comprises measuring the volume of the sample in the area imaged by the reading device.

20-13. The method of embodiment 20, wherein the first plate comprises a plurality of binding sites that each comprise:

(i) proximity-dependent signal amplification layer, and (ii) capture agents that are attached to the proximity-dependent signal amplification layer.

20-14. The method of embodiment 20, wherein the target analyte is a protein, peptide, DNA, RNA, nucleic acid, small molecule, cell, or nanoparticle.

20-15. The method of any prior method embodiment, wherein the capture agent specifically binds to the target analyte.

20-16. The method of any prior method embodiment, wherein the image shows the position, local intensity, and local spectrum of the signals.

20-17. The method of any prior method embodiment, wherein the signals are luminescence signals selected from the group consisting of fluorescence, electroluminescence, chemiluminescence, and electrochemiluminescence signals.

20-18. The method of any prior method embodiment, wherein the signals are Raman scattering signals.

20-20. The method of any prior method embodiment, wherein the signals are the forces due to local electrical, local mechanical, local biological, or local optical interaction between the plate and the reading device.

20-21. The method of any prior method embodiment, wherein before the step (b), it further comprises a step of labeling the target analytes with a label, either prior to or after they are bound to said capture agent.

20-22. The method of any prior method embodiment, wherein the reading step (b) is performed by applying a voltage bias between said signal amplification layer and another electrode, thereby providing greater sensitivity.

20-23. The method of any prior method embodiment, wherein the identifying and counting step (c) comprises: (1) determining the local intensity of background signal, (2) determining local signal intensity for one label, two labels, three labels, and four or more labels; and (3) determining the total number of labels in the imaged area.

20-24. The method of any prior method embodiment, wherein the identifying and counting step (c) comprises: (1) determining the local spectrum of background signal, (2) determining local signal spectrum for one label, two labels, three labels, and four or more labels; and (3) determining the total number of labels in the imaged area.

20-25. The method of any prior method embodiment, wherein the identifying and counting step (c) comprises: (1) determining the local Raman signature of background signal, (2) determining local signal Raman signature for one label, two labels, three labels, and four or more labels; and (3) determining the total number of labels in the imaged area.

20-26. The method of any prior method embodiment, wherein the identifying and counting step comprises determining one or more of the local intensity, spectrum, and Raman signatures.

20-27. The method of any prior method embodiment, wherein the binding step (a) is accelerated by applying an electric field to the plate, thereby moving the analytes to the sensing amplification layer.

20-28. The method of any prior method embodiment, wherein the proximity-dependent signal amplification layer comprises a D2PA.

20-29. The method of any prior embodiment, wherein the proximity-dependent signal amplification layer comprises one or a plurality of metallic discs and a significantly flat metallic film, wherein a substantial portion of the metallic disc has a separation from the metallic film and the separation and the dimensions of the disks are less than the wavelength of the light used in sensing.

20-30. The method of embodiment 20-29, wherein the metallic disk has a shape selected from the group of shapes consisting of round, polygonal, pyramidal, elliptical, elongated bar shaped, or any combination thereof.

20-31. The method of embodiment 20-29, wherein the separation is 0.5 to 30 nm, and wherein the discs have an average lateral dimension in the range of 20 nm to 250 nm.

20-32. The method of any prior method embodiment, wherein the capture agents are attached to the sensing amplification layer through a molecular linking layer that links said capture agents with said sensing amplification layer.

20-33. The method of any prior method embodiment, wherein the signals are light signals.

20-34. The method of any prior method embodiment, wherein the signals are produced by a fluorescent label, that is associated with the bound analyte, either before or after binding of the analyte to the capture agent.

20-35. The method of any prior method embodiment, wherein the average distance between the two adjacent signals being read to form the image of signals in reading step (c) is greater than 10 nm.

20-36. The method of any prior method embodiment, wherein the signals are signals generated by Raman scattering.

20-37. The method of any prior method embodiment, wherein the capture agent is an antibody.

20-38. The method of any prior method embodiment, wherein the capture agent is a polynucleotide.

Further Additional Embodiments

A "capture component", as used herein, is any molecule, other chemical/biological entity or solid support modification disposed upon a solid support that can be used to specifically attach, bind or otherwise capture a target molecule or particle (e.g., an analyte molecule or dissociated species), such that the target molecule/particle becomes immobilized with respect to the capture component and solid substrate. As used herein, "immobilized" means captured, attached, bound, or affixed so as to prevent dissociation or loss of the target molecule/particle, but does not require absolute immobility with respect to either the capture component or the solid substrate. Capture components which are useful or potentially useful for practicing certain aspects and embodiments of the invention are discussed in more detail below. At least some of the analyte molecules, upon exposure to the substrate comprising a plurality of capture components, can become immobilized with respect to a capture component, thereby forming a plurality of immobilized complexes. For example, in certain embodiments, substantially all of the plurality of analyte molecules may become immobilized with respect to capture components such that essentially each of the plurality of immobilized complexes comprises a capture component and an analyte molecule.

A "binding ligand," as used herein, is any molecule, particle, or the like which specifically binds to or otherwise specifically associates with an analyte molecule, immobilized complex and/or dissociated species or another molecule or particle bound to or otherwise associated with the analyte molecule, immobilized complex and/or dissociated species (e.g., another binding ligand). In certain embodiments, the binding ligand can convert a precursor labeling agent molecule to a labeling agent, as discussed more below. More than one type of binding ligand may be employed in any given assay method, for example, a first type of binding ligand and a second type of binding ligand. In one example, the first binding ligand is able to associate with an analyte molecule and the second binding ligand is able to associate with the first binding ligand. When the substrate is exposed to a plurality of types of binding ligand, at least some of the plurality of immobilized complexes may additionally comprise, in some cases, at least one of each type of binding ligand. In certain embodiments, the binding ligand can be exposed to the substrate after capture of the analyte molecule so that the binding ligand binds to the immobilized complex. In other embodiments, the binding ligand may become associated with the analyte molecule to form a complex followed by capture of the complex by the substrate to form the immobilized complex. In yet other embodiments, the binding ligand may bind to the dissociated species formed upon release of the immobilized complex, or portion thereof, from the substrate.

In some embodiments, the immobilized complex comprises a cleavable linkage. A "cleavable linkage," as used herein, is linkage that is able to be readily (i.e. Under conditions not detrimental to the integrity of other portions of the immobilized complex) and selectively cleaved upon exposure to a dissociating agent. The cleavable linkage upon cleavage by exposure to a dissociating agent forms the dissociated species. One specific example of a cleavable linkage, which can be cleaved using beta-mercaptoethanol, is a disulfide linkage. Cleavable linkages and corresponding dissociating agents that can cause the cleavable linkage to cleave are discussed in more detail below.

In some embodiments, the plurality of molecules may be released from the first substrate by exposure to a dissociating agent. For example, a substrate comprising a plurality of capture components may be exposed to a sample comprising a plurality of analyte molecules or particles, such that analyte molecules or particles associate with capture components to form a plurality of complexes, which are immobilized with respect to the substrate. Each of the immobilized complexes may comprise at least one capture component and at least one analyte molecule or particle. Exposure of the plurality of immobilized complexes to a reducing agent (e.g., beta-mercaptoethanol, dithiothreitol, tris(2-carboxyethyl)phosphine, etc.) Causes at least a portion of at least some of the plurality of immobilized complexes to dissociate from the substrate to form a plurality of dissociated species. At least some of the dissociated species may be detected to determine the presence of and/or a measurement of the amount or concentration of the analyte molecules or particles in the fluid sample, as discussed more herein. The reducing agent may or may not be removed form the solution comprising the dissociated species prior to detection of the dissociated species, as discussed more herein. In some embodiments, the dissociating agent is a reducing agent (e.g., beta-mercaptoethanol). In some embodiments, the dissociating agent has essentially no specific affinity for the capture components. That is, the dissociating agent does not bring about release of the dissociating species by interacting with the capture component and employing competitive binding to release the analyte molecule that associated with the capture component.

In some embodiments, the plurality of dissociated species may be formed by cleavage of cleavable linkages. For example, each of the immobilized complexes may comprise at least one cleavable linkage (e.g., a disulfide linkage). The cleavable linkage may located in a capture component, analyte molecule or a binding ligand and may be cleaved to form a plurality of dissociated species. In a embodiment, the cleavable linkage is a disulfide linkage which may, in some cases, be cleaved by exposure of the immobilized complexes to a reducing agent.

In some embodiments, at least a portion of an immobilized complex comprises an enzymatic component. That is, at least one of the capture component, the analyte molecule or any additional components of the immobilized complex (e.g., binding ligand(s)) comprises an enzymatic component. In some cases, the enzymatic component may be in the portion of the immobilized complex which is dissociated from the first substrate to form a dissociated species. For example, FIG. 9 illustrate an exemplary embodiment of an assay wherein the binding ligand comprises a moiety (e.g., an enzymatic component), as discussed more herein.

In certain embodiments, the protocol may include the use of at least one binding ligand, at least a portion of which comprises at least a portion of the dissociated species transferred from the first substrate to the second substrate (e.g., the binding ligand may be immobilized prior to release or following release of the molecules or particles from the first substrate). In some embodiments, the binding ligand comprises a cleavable linkage (e.g., a disulfide linkage) and/or is dissociated from the first substrate by exposure to a reducing agent. In some embodiments, at least one binding ligand comprises an enzymatic component. For example, the binding ligand(s), or at least the portions thereof forming at least a portion of the dissociated species transferred from the first substrate to the second substrate, may further comprise a moiety (e.g., an enzymatic component or enzyme substrate) able to convert a precursor labeling agent molecule (e.g., an enzymatic substrate) into a labeling agent (e.g., a detectable product). After transfer of and, optionally, capture of the dissociated species on or within the second substrate, the second substrate may be exposed to a plurality of precursor labeling agent molecules, wherein the plurality of precursor labeling agent molecules are converted to a plurality of labeling agent molecules upon exposure to a binding ligand. A measure of the concentration of the analyte molecules or particles in the fluid sample can then be determined based on the measurement of the labeling agent molecules on or within the second substrate.

A method of detecting analyte molecules or particles in QMAX device, comprising:

(a) obtaining a sample comprising a plurality of analyte molecules or particles;

(b) obtaining a QMAX device that comprises:

a first plate, a second plate, and spacers, wherein:

i. the plates are movable relative to each other into different configurations;

ii. one or both plates are flexible;

iii. one or both plates have a plurality of reaction vessels;

iv. each of the plates comprises an inner surface that has a sample contact area for contacting a blood sample;

v. one or both of the plates comprising a plurality of capture components;

vi. one or both of the plates comprise the spacers that are permanently fixed on the sample contact area of a respective plate;

vii. the spacers have:

(1) a predetermined substantially uniform height that has a value selected in the range of 1 um to 80 um, (2) a shape of pillar with substantially uniform cross-section and a flat top surface;

(3) a ratio of the width to the height equal or larger than one;

(4) a predetermined fixed, non-random, inter-spacer distance that is in the range of 10 um to 200 um (micron); and (c) depositing the sample on one or both of the plate, exposing the plate comprising a plurality of capture components to a sample comprising a plurality of analyte molecules or particles, so that analyte molecules or particles associate with capture components to form a plurality of complexes, each complex being immobilized with respect to the plate and comprising at least one capture component and at least one analyte molecule or particle;

(d) dissociating at least a portion of each complex to form a plurality of dissociated species, which are not immobilized with respect to the plate;

(e) partitioning the plurality of dissociated species across a plurality of reaction vessels;

(f) determining the presence or absence of a dissociated species in at least one reaction vessel;

(g) determining the number of the plurality of reaction vessels and/or fraction of the plurality of reaction vessels that contain or do not contain a dissociated species, wherein the plurality of dissociated species are partitioned such that a statistically significant fraction of the reaction vessels contain no dissociated species and a statistically significant fraction of reaction vessels contain at least one dissociated species.

A method for determining a measure of the concentration of analyte molecules or particles in a fluid sample, comprising:

capturing a plurality of analyte molecules or particles on a first plate;

releasing a plurality of molecules or particles from the first plate;

detecting molecules or particles released from the first plate on or within a second plate comprising a plurality of reaction vessels;

and determining a measure of the concentration of the analyte molecules or particles in the fluid sample based on the detection of molecules or particles released from the first plate on or within the second plate, wherein the measure of the concentration of the analyte molecules or particles in the fluid sample is determined by determining the number or fraction of the plurality of reaction vessels that contain or do not contain a molecule or particle released from the first plate.

The method or device of any prior embodiment, wherein the number or fraction of the plurality of reaction vessels that contain a dissociated species is related to the concentration of analyte molecules or particles in the sample.

The method or device of any prior embodiment, further comprising an act of determining the concentration of analyte molecules or particles in the fluid sample.

The method or device of any prior embodiment, wherein the plate comprises a plurality of beads.

The method or device of any prior embodiment, wherein the beads are magnetic.

The method or device of any prior embodiment, wherein the plate comprises a microtiter plate.

The method or device of any prior embodiment, wherein the plurality of reaction vessels are formed upon the mating of at least a portion of a sealing component and at least a portion of a second plate.

The method or device of any prior embodiment, wherein the plurality of reaction vessels are defined on a planar second plate.

The method or device of any prior embodiment, wherein the volume of each of the plurality of reaction vessels is between about 10 attoliters and about 100 picoliters.

The method or device of any prior embodiment, wherein each of the plurality of reaction vessels comprise at least one dissociated species capture component.

The method or device of any prior embodiment, further comprising immobilizing at least one of the plurality of dissociated species with respect to the at least one dissociated species capture component.

The method or device of any prior embodiment, wherein each of the plurality of reaction vessels is exposed to at least one precursor labeling agent molecule.

The method or device of any prior embodiment, wherein the at least one precursor labeling agent molecule is converted to a labeling agent molecule when contained in a reaction vessel comprising a dissociated species.

The method or device of any prior embodiment, wherein the presence or absence of a dissociated species in a reaction vessel is determined by determining the presence or absence of a labeling agent molecule in the reaction vessel.

The method or device of any prior embodiment, wherein the plate is exposed to a plurality of first binding ligands.

The method or device of any prior embodiment, wherein a first binding ligand associates with each of the plurality of analyte molecules or particles in the exposing act to form at least a portion of the plurality of complexes.

The method or device of any prior embodiment, wherein each first binding ligand comprises an enzymatic component.

The method or device of any prior embodiment, wherein the first binding ligand comprises a cleavable linkage.

The method or device of any prior embodiment, wherein the plurality of dissociated species is formed by cleaving at least some of the cleavable linkages.

The method or device of any prior embodiment, wherein at least one of the plurality of dissociated species comprises at least a portion of a first binding ligand.

The method or device of any prior embodiment, wherein the plurality of dissociated species are formed by exposing the plate to electromagnetic radiation.

The method or device of any prior embodiment, wherein the plurality of dissociated species are formed by exposing the plate to a dissociating agent.

The method or device of any prior embodiment, wherein the dissociating agent comprises at least one of a pH agent, salt agent, denaturing agent, reducing agent, chemical agent, or enzyme.

The method or device of any prior embodiment, wherein the analyte molecules or particles are proteins.

The method or device of any prior embodiment, wherein the capture component is an antibody.

The method or device of any prior embodiment, further comprising sealing the plurality of reaction vessels.

The method or device of any prior embodiment, wherein the first plate comprises a plurality of first capture components.

The method or device of any prior embodiment, wherein at least one of the plurality of analyte molecules or particles is captured by being specifically immobilized with respect to at least one of the plurality of first capture components.

The method or device of any prior embodiment, further comprising the act of exposing the plurality of analyte molecules or particles captured on the first plate to a plurality of first binding ligands.

The method or device of any prior embodiment, wherein at least one of the plurality of first binding ligands becomes immobilized with respect to each of at least a fraction of the plurality of analyte molecules or particles captured on the first plate.

The method or device of any prior embodiment, wherein the releasing act comprises exposing the plate to electromagnetic radiation.

The method or device of any prior embodiment, wherein the releasing act comprises exposing the plate to a dissociating agent.

The method or device of any prior embodiment, wherein the second plate comprises a plurality of second capture components.

The method or device of any prior embodiment, wherein each of at least a fraction of the plurality of molecules or particles released from the first plate become immobilized with respect to at least one second capture component on the second plate.

The method or device of any prior embodiment, further comprising an act of sealing at least a fraction of the plurality of reaction vessels.

The method or device of any prior embodiment, wherein the measure of the concentration of the analyte molecules or particles in the fluid sample is determined at least in part by a Poisson distribution analysis of the number or fraction of the plurality of reaction vessels that contain an analyte molecule or particle released from the plate.

The method or device of any prior embodiment, wherein less than about 80% of the total number of the plurality of reaction vessels contain at least one analyte molecule or particle released from the plate.

The method or device of any prior embodiment, wherein the second plate comprises a planar surface and a sealing component comprising a plurality of microwells, and the plurality of reaction vessels are formed upon mating of at least a portion of the planar plate with at least a portion of the sealing component.

Beads with Different Color Code for Multiplexing:

The devices or methods of any prior embodiment, wherein the label is beads containing color bar-code.

The devices or methods of any prior embodiment, wherein the beads with one kind of color bar-codes contains reagent that have affinity for one kind of analyte.

The devices or methods of any prior embodiment, wherein the number of beads of each kind of bar-code that captures specific kind of analyte are statistical significant.

The devices or methods of any prior embodiment, wherein the label is beads with different geometric sizes, wherein the sizes include, but not limited to, sphere, cube, cuboid, tetrahedron.

The devices or methods of any prior embodiment, wherein the microwells have different geometric shape, wherein each one shape of microwell can only accommodate one geometric size of beads The devices or methods of any prior embodiment, wherein the beads with different geometric sizes contains capture agent for different analyte.

The devices or methods of any prior embodiment, wherein the number of beads of each individual geometric size that captures specific analyte are statistical significant.

The devices or methods of any prior embodiment wherein quantification can be done using the ratio of the number of labels to the number of spacer/pillars.

A method for determining a measure of the concentration of analyte molecules or particles in a fluid sample on QMAX card, comprising:

Perform assay on QMAX card using beads as label;

Determining a measure of the concentration of analyte in the sample based on the ratio of the number of beads determined to bound with analyte molecule to the number of spacers (pillars).

Other Embodiments of Present Invention and Related Disclosures

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate (ISD$^4$/(hE)) is 5×10$^6$ um$^3$/GPa or less.

The method or device of any prior embodiment, wherein the fourth power of the inter-spacer-distance (ISD) divided by the thickness (h) and the Young's modulus (E) of the flexible plate (ISD$^4$/(hE)) is 5×10$^5$ um$^3$/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is 5×10$^6$ um$^3$/GPa or less.

The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the analytes is proteins, peptides, nucleic acids, synthetic compounds, or inorganic compounds.

The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior embodiment, wherein the spacers have a shape of pillars and a ratio of the width to the height of the pillar is equal or larger than one.

The method of any prior embodiment, wherein the sample that is deposited on one or both of the plates has an unknown volume.

The method or device of any prior embodiment, wherein the spacers have a shape of pillar, and the pillar has substantially uniform cross-section.

The method or device of any prior embodiment, wherein the samples is for the detection, purification and quantification of chemical compounds or biomolecules that correlates with the stage of certain diseases.

The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

The method or device of any prior embodiment, wherein the samples is related to the detection, purification and quantification of microorganism.

The method or device of any prior embodiment, wherein the samples is related to virus, fungus and bacteria from environment, e.g., water, soil, or biological samples.

The method or device of any prior embodiment, wherein the samples is related to the detection, quantification of chemical compounds or biological samples that pose hazard to food safety or national security, e.g. toxic waste, anthrax.

The method or device of any prior embodiment, wherein the samples is related to quantification of vital parameters in medical or physiological monitor.

The method or device of any prior embodiment, wherein the samples is related to glucose, blood, oxygen level, total blood count.

The method or device of any prior embodiment, wherein the samples is related to the detection and quantification of specific DNA or RNA from biosamples.

The method or device of any prior embodiment, wherein the samples is related to the sequencing and comparing of genetic sequences in DNA in the chromosomes and mitochondria for genome analysis.

The method or device of any prior embodiment, wherein the samples is related to detect reaction products, e.g., during synthesis or purification of pharmaceuticals.

The method or device of any prior embodiment, wherein the samples is cells, tissues, bodily fluids, and stool.

The method or device of any prior embodiment, wherein the sample is the sample in the fields of human, veterinary, agriculture, foods, environments, and drug testing.

The method or device of any prior embodiment, wherein the sample is a biological sample is selected from hair, finger nail, ear wax, breath, connective tissue, muscle tissue, nervous tissue, epithelial tissue, cartilage, cancerous sample, or bone.

The devices or methods of any prior embodiment, wherein the inter-spacer distance is in the range of 5 □m to 120 □m.

The devices or methods of any prior embodiment, wherein the inter-spacer distance is in the range of 120 □m to 200 □m.

The device of any prior device embodiment, wherein the flexible plates have a thickness in the range of 20 um to 250 um and Young's modulus in the range 0.1 to 5 GPa.

The device of any prior device embodiment, wherein for a flexible plate, the thickness of the flexible plate times the Young's modulus of the flexible plate is in the range 60 to 750 GPa-um.

The device of any prior device embodiment, wherein the layer of uniform thickness sample is uniform over a lateral area that is at least 1 mm$^2$.

The device of any prior device embodiment, wherein the layer of uniform thickness sample is uniform over a lateral area that is at least 3 mm$^2$.

The device of any prior device embodiment, wherein the layer of uniform thickness sample is uniform over a lateral area that is at least 5 mm$^2$.

The device of any prior device embodiment, wherein the layer of uniform thickness sample is uniform over a lateral area that is at least 10 mm$^2$.

The device of any prior device embodiment, wherein the layer of uniform thickness sample is uniform over a lateral area that is at least 20 mm$^2$.

The device of any prior device embodiment, wherein the layer of uniform thickness sample is uniform over a lateral area that is in a range of 20 mm$^2$ to 100 mm$^2$.

The device of any prior device embodiment, wherein the layer of uniform thickness sample has a thickness uniformity of up to +/−5% or better.

The device of any prior device embodiment, wherein the layer of uniform thickness sample has a thickness uniformity of up to +1-10% or better.

The device of any prior device embodiment, wherein the layer of uniform thickness sample has a thickness uniformity of up to +1-20% or better.

The device of any prior device embodiment, wherein the layer of uniform thickness sample has a thickness uniformity of up to +/−30% or better.

The present invention find use in a variety of different applications in various fields, where determination of the presence or absence, and/or quantification of one or more analytes in a sample are desired. For example, the present inventions finds use in the detection of atoms, molecules, proteins, peptides, nucleic acids, synthetic compounds, inorganic compounds, organic compounds, bacteria, virus, cells, tissues, nanoparticles, and the like. The sample can be a sample in various fields, that include, but not limited to, human, veterinary, agriculture, foods, environments, health, wellness, beauty, and others.

Present Embodiments

A device for performing a digital assay comprising:

a first plate, a second plate, and microwells, wherein:

(c) the first and second plates are movable relative to each other into different configurations, and have, on its respective surface, a sample contact area for contacting the fluidic sample that containing an analyte;

(d) the second plate has, in the sample contact area, a plurality of the microwells, wherein each microwell has (i) predetermined and known geometry, (ii) a well depth of 200 um or less, and (iii) has a volume substantially less than that of the fluidic sample, wherein one of the configurations is an open configuration, in which: the average spacing between the inner surface of the first plate and the rim of the microwells in the second plate is larger than the depth of the well and the sample is deposited on one or both of the plates; and wherein another of the configurations is a closed configuration, which is the configuration after the sample is deposited in the open configuration; in the closed configuration, at least a part of the sample is inside the microwells, and the average spacing between the inner surface of the first plate and the rim of the microwell in the second plate is less than 1 um or less than 1/10 (one tenth) of the microwell depth.

An apparatus comprising a thermal cycler and a device of embodiment 1.

An apparatus comprising a thermal cycler, a device of embodiment 1, and a reader for real-time PCR.

A method for partitioning a fluidic sample, comprising:

obtaining a device or apparatus of any of any prior embodiment, depositing a sample on one or both of the plates when the plates are in an open configuration, wherein the deposition is in the form of a single or multiple droplet of the sample, wherein at least one of the droplets has a volume that occupies more than two microwells; and closing the plates to the closed configuration to partition the sample in the microwells.

The device, apparatus or method of any prior embodiment, wherein the analyte is protein, peptide, nucleic acids, virus, bacterial, cell, nanoparticle, molecule, synthetic compounds, or inorganic compounds.

The device, apparatus or method of any prior embodiment, further comprising spacers that are configured to regulate the spacing between the first and second plates.

The device, apparatus or method of any prior embodiment, further comprising a binding site that is either on the inner surface of one or both of the plates, wherein the binding site comprises a capture agent immobilized at the site, and the capture agent is configured to specifically capture an analyte in the sample.

The device, apparatus or method of any prior embodiment, further comprising a surface amplification layer that is either on the inner surface of one or both of the plates, wherein the surface amplification layer comprises a capture agent immobilized at the site, and the capture agent is configured to specifically capture an analyte in the sample, wherein the surface amplification layer amplifies an optical signal from the analyte or a label attached to the analyte much stronger when they are is in proximity of the surface amplification layer than that when they are micron or more away.

The device, apparatus or method of any prior embodiment, wherein the amplification factor of the surface amplification layer is adjusted to make the optical signal from a single label that is bound directly or indirectly to the capture agents visible.

The device, apparatus or method of any prior embodiment, wherein the amplification factor of the surface amplification layer is adjusted to make the optical signal from a single label that is bound directly or indirectly to the capture agents visible.

The device, apparatus or method of any prior embodiment, wherein device further comprise reagents that are in the microwell in a close configuration of the plate, wherein the reagents will generate, when there is a binding between the analyte and a detection agent, multiple light emitting components in the well, whereas the detection agent specifically binds to the analyte.

The device, apparatus or method of any prior embodiment, wherein the spacing between the first plate and the second plate in the closed configuration is configured to make saturation binding time of the target analyte to the capture agents 300 sec or less.

The device, apparatus or method of any prior embodiment, wherein the spacing between the first plate and the second plate in the closed configuration is configured to make saturation binding time of the target analyte to the capture agents 60 sec or less.

The device, apparatus or method of any prior embodiment, wherein the amplification factor of the surface amplification layer is adjusted to make the optical signal from a single label visible.

The device, apparatus or method of any prior embodiment wherein the capture agent is a nucleic acid.

The device, apparatus or method of any prior embodiment wherein the capture agent is a protein.

The device, apparatus or method of any prior embodiment wherein the capture agent is an antibody.

The device, apparatus or method of any prior embodiment wherein the capture agent is an aptamer.

The device, apparatus or method of any prior embodiment wherein the capture agent is an aptamer.

The device, apparatus or method of any prior embodiment, further comprising a storage site that is either on the inner surface of one or both of the plates, wherein the storage site comprises a reagent that can be dissolved into a liquid.

The device, apparatus or method of any prior embodiment wherein the reagents are for amplification of an analyte in the sample.

The device, apparatus or method of any prior embodiment wherein the reagents amplify the analyte by polymerase chain reaction (PCR).

The device, apparatus or method of any prior embodiment wherein the reagents are detections reagents.

The device, apparatus or method of any prior embodiment wherein the volume of each well is configured, for an expected target analyte concentration, so that the distribution of target analyte in each well that is filled with the sample follows Poisson distribution.

The device, apparatus or method of any prior embodiment wherein the volume of each well is configured, for an expected target analyte concentration, so that the distribution of target analyte in each well that is filled with the sample is, on average, one target analyte per every 2 wells, 3 wells, 5 wells, 10 wells, 20 wells, 0 wells, 50 wells, 75 wells, 100 wells, 150 wells, 200 wells, 300 wells, 500 wells, 1000 wells, 2000 wells, 10000 wells, 100,000 wells, or in a range of any two value.

The device, apparatus or method of any prior embodiment wherein the volume of each well is configured preferably, for an expected target analyte concentration, so that the distribution of target analyte in each well that is filled with the sample is, on average, one target analyte per every 10 wells, 20 wells, 0 wells, 50 wells, 75 wells, 100 wells, or in a range of any two value.

The device, apparatus or method of any prior embodiment, wherein, in the closed configuration, the average spacing between the inner surface of the first plate and the rim of the microwell in the second plate is less than $\frac{1}{11}$ (one eleventh), $\frac{1}{20}$, $\frac{1}{30}$, $\frac{1}{40}$, $\frac{1}{50}$, $\frac{1}{100}$, $\frac{1}{300}$, $\frac{1}{500}$ of the microwell depth, or in a range of any two values.

The device, apparatus or method of any prior embodiment, wherein, in the closed configuration, the inner surface of the first plate and the rim of the microwell in the second plate are significantly in contact.

The device, apparatus or method of any prior embodiment, wherein, in the closed configuration, the average spacing between two neighboring wells is less than 5 nm, 10 nm, 30 nm, 50 nm, 100 nm, 200 nm, 500 nm, 1 um, 2 um, 5 um, 10 um, 20 um, 50 um, 100 um, or in a range of any two values.

The device, apparatus or method of any prior embodiment, wherein the microwells have a shape selected from round, rectangle, hexagon, and/or any other polyhedron, with lattice of square, hexagon, and/or any other lattices.

The device, apparatus or method of any prior embodiment, wherein the wells on the first plate have a period (average well to well center distance) of at least 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

The device, apparatus or method of any prior embodiment, wherein the wells on the first plate have well size (average length or diameter) of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um.

The device, apparatus or method of any prior embodiment, wherein the wells on the first plate have a depth of at least 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um. The device, apparatus or method of any prior embodiment, wherein the wells have (i) no metal coating (ii) metal coating on bottom of the well (top of the pillar) (iii) metal coating on side wall of the well (side of the pillar) and/or (iv) metal coating on both bottom and side wall of the well.

The device, apparatus or method of any prior embodiment, wherein the metal is gold, aluminum, silver, copper, tin and/or any combination thereof.

The device, apparatus or method of any prior embodiment, the well area ratio (the ratio of the well area to the total area of the surface) is 40% to 50%, 50% to 60%, 60% to 70%, 70% to 80%, 80% to 90%, 90% to 99%.

The device, apparatus or method of any prior embodiment, wherein the well edge to well edge distance is larger than the well depth, which is to make sure the diffusion time of well edge to well edge is longer than the diffusion time of well edge to bottom of the well.

The device, apparatus or method of any prior embodiment, wherein the dimensions of the wells are designed to make sure no cross-reaction taking place during the assay process.

The device, apparatus or method of any prior embodiment, wherein the number of wells on the first plate is much larger than the molecule numbers in the sample.

The device, apparatus or method of any prior embodiment, wherein the total well number on the first plate is 1 to 2 times, 2 to 5 times, 5 to 10 times, 10 to 100 times, 100 to 1000 times, 1000 to 10000 times of 600, if the molecule concentration is about 1 fM/uL.

The device, apparatus or method of any prior embodiment, wherein the total well number on the first plate is 1 to 2 times, 2 to 5 times, 5 to 10 times, 10 to 100 times, 100 to 1000 times, 1000 to 10000 times of 600,000, if the molecule concentration is about 1 pM/uL.

The device, apparatus or method of any prior embodiment, wherein the total well number on the first plate is 1 to 2 times, 2 to 5 times, 5 to 10 times, 10 to 100 times, 100 to 1000 times, 1000 to 10000 times of 600,000,000, If the molecule concentration is about 1 nM/uL.

The device, apparatus or method of any prior embodiment, wherein the number of wells allows for no more than one target molecule being placed in a well after closing the device.

The device, apparatus or method of any prior embodiment, wherein at least one of the plates comprises an amplification surface.

The device, apparatus or method of any prior embodiment, wherein the device further comprises a thin sealer layer between the first plat and the second plate, wherein in a closed configuration, the sealer is configured to prevent a sample or an analyte in one microwell from moving to other microwells.

The device, apparatus or method of any prior embodiment, wherein the device further comprises a clamp, wherein in a closed configuration, the embodiment is configured to prevent a sample or an analyte in one microwell from moving to other microwells.

The device, apparatus or method of any prior embodiment, wherein the signal amplification layer comprises a layer of metallic material.

The device, apparatus or method of any prior embodiment, wherein the signal amplification layer comprises a layer of metallic material and a dielectric material on top of the metallic material layer, wherein the capture agent is on the dielectric material.

The device, apparatus or method of any prior embodiment, wherein the metallic material
layer is a uniform metallic layer, nanostructured metallic layer, or a combination.

The device, apparatus or method of any prior embodiment, wherein the amplification layer comprises a layer of metallic material and a dielectric material on top of the metallic material layer, wherein the capture agent is on the dielectric material, and the dielectric material layer has a thickness of 0.5 nm, 1 nm, 5 nm, 10 nm, 20 nm, 50 nm, 00 nm, 200 nm, 500 nm, 1000 nm, 2 um, 3 um, 5 um, 10 um, 20 um, 30 um,50 um, 100 um, 200 um, 500 um, or in a range of any two values.

The device, apparatus or method of any prior embodiment, wherein the sample is deposited en masse on one or both of the plates and the closing step spreads the sample over and into at least some of the microwells.

The device, apparatus or method of any prior embodiment, wherein the method comprises depositing the sample on a plate, pressing the second plate and isolating the sample into wells, counting the wells filled with the sample, calculating the volume of the sample, counting the wells with a signal, and calculating the concentration of the analyte in the sample.

The device, apparatus or method of any prior embodiment, wherein the method comprises identifying which wells are not filled with sample.

The device, apparatus or method of any prior embodiment, further comprising the step of measuring, while the plates are in a closed configuration, a signal related to a target analyte in each of the microwells.

The device, apparatus or method of any prior embodiment, wherein the method comprises amplification, wherein the amplification makes the analyte more observable than that without the amplification, and wherein the amplification comprises chemiluminescence, luminescence, nucleic acid amplification, ELISA (enzyme-linked immunosorbent assay), light enhancement using plasmonic structures or a chemical reaction.

The device, apparatus or method of any prior embodiment, further comprising counting the number of wells that comprise the target analyte.

The device, apparatus or method of any prior embodiment, wherein statistically each well will have no more than one molecule of the target analyte.

The device, apparatus or method of any prior embodiment, wherein the distribution of target analyte in each well that is filled with the sample follows Poisson distribution.

The device, apparatus or method of any prior embodiment, further comprising determining the concentration of the target analyte in the sample.

The device, apparatus or method of any prior embodiment, wherein the target analyte is a protein, a nucleic acid, small molecule, cell or particle.

The device, apparatus or method of any prior embodiment, wherein the target analyte is a nucleic acid, and the method comprises amplifying the nucleic acid.

The device, apparatus or method of any prior embodiment, wherein the amplifying is done by polymerase chain reaction (PCR).

The device, apparatus or method of any prior embodiment, wherein the target analyte is assayed using a binding assay.

The device, apparatus or method of any prior embodiment, further comprising washing unbound target analyte from the device.

The device, apparatus or method of any prior embodiment, wherein the method further comprises, separating the two plates partially or entirely after they have been closed, washing way the original sample or adding an another reagent, and then a step of bring the plates into a closed configuration.

The device, apparatus or method of any prior embodiment, wherein the washing is done using a sponge.

The device, apparatus or method of any prior embodiment, wherein the method further comprises imaging of the sample contacting area.

The device, apparatus or method of any prior embodiment, wherein the imaging of the sample contacting area measures the lump-sum signal related to the analyte from the sample contact area.

The device, apparatus or method of any prior embodiment, wherein the imaging of the sample contacting area measures individual signal caused by the individual binding event between a capture agent and a captured target analyte.

The device, apparatus or method of any prior embodiment, wherein the imaging of the sample contacting area measures both (a) the lump-sum signal related to the analyte from the sample contact area and (b)individual signal caused by the individual binding event between a capture agent and a captured target analyte.

The device, apparatus or method of any prior embodiment, wherein the existence or concentration of a target analyte in the sample is determined from the detection of the individual signal caused by the individual binding event between a capture agent and the captured target analytes.

The device, apparatus or method of any prior embodiment, wherein the method comprises of subtracting air-pockets in determining the actual sample volume, by (i) identifying the empty wells by imaging wells in a bright field image and/or by imaging before the amplification step, and (ii) subtracting the empty well in volume calculation in quantify the analyte concentration.

Uses

Among other things, the present method may be used to detect and/or measure the amount of a diagnostic biomarker that is associated with a disease such as cancer, infection, or inflammatory disease (see, e.g., Tables 1-3 of WO2017058827), an autoantibody epitope (see Table 4 of WO2017058827), an allergen epitope (see Table 5 of WO2017058827), an infectious agent (see, e.g., Table 6 of WO2017058827), a miRNA (see, e.g., Table 7 of WO2017058827), an environmental marker (see, e.g., Table 8 of WO2017058827), a foodstuff markers (see, e.g., Table 9 of WO2017058827), a small molecule such as a metabolite or a drug (e.g., THC—COOH (11-nor-9-carboxy-THC)), one or molecules in cell free DNA (cfDNA), including circulating tumor DNA (ctDNA), one or molecules in cell free RNA (cfRNA), and cells, e.g., circulating tumor cells, viruses or bacteria, etc.

In some embodiments, sample is a bodily fluid or a processed form thereof. Bodily fluids of interest include plasma, saliva and urine, although several other bodily fluids may be used in the present method. Bodily fluids include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, and urine. In some embodiments, a sample may be obtained from a subject, e.g., a human, and it may be processed prior to use in the subject assay. For example, prior to analysis, the protein may be extracted from a tissue sample prior to initiating the present method. In particular embodiments, the sample may be a clinical sample, e.g., a sample collected from a patient.

The present method may have a sensitivity of at least 5 fM, 10 fM, 50 fM, 100 fM, 0.5 pM, 1 pM, 5 pM, 10 pM, 50 pM, 100 pM, 0.5 nM, 1 nM, 5 nM, 10 nM, 50 nM or 100 nM depending on the target analyte.

Without wishing to be bound to any particular use, the present method has particular utility in analyzing blood plasma. Blood plasma can be obtained non-invasively and it contains a variety of different, low abundance proteins that are diagnostic, prognostic or theranostic (see, generally, Anderson et al., Molecular & Cellular Proteomics 2002 1: 845-867 and Anderson et al., Clinical Chemistry 2010 56: 177-185). As such, in some embodiments, the present method may be used to quantify any one or combination (e.g., 2, 3, 4, 5 or more) of the following proteins in plasma: acid phosphatase, IgG, alanine aminotransferase (ALT or SGPT), IgM, albumin, inhibin-A, aldolase, insulin, alkaline phosphatase (ALP), insulinlike growth factor-I (IGF-I), α-1-acid glycoprotein (orosomucoid), insulinlike growth factor-II (IGF-II), α-1-antitrypsin, IGFBP-1, α-2-antiplasmin, IGFBP-3, α-2-HS-glycoprotein, interleukin-2 receptor (IL-2R), α-2-macroglobulin, isocitric dehydrogenase, α-feto-protein (tumor marker), K light chains, amylase, lactate dehydrogenase heart fraction (LDH-1), amylase, lactate dehydrogenase liver fraction (LLDH), ACE, lactoferrin, antithrombin III (ATIII), A light chains, apolipoprotein A1, lipase, apolipoprotein B, Lp(a), aspartate aminotransferase (AST or SGOT), lipoprotein-associated phospholipase A2 (LP-PLA2), 3-2 microglobulin, LH, 3-thromboglobulin, lysozyme, biotinidase, macrophage migration inhibitory factor (MIF) myeloperoxidase (MPO), cancer antigen 125 (CA 125), myoglobin, cancer antigen 15-3 (CA 15-3), osteocalcin, cancer antigen, human epididymis protein (HE4), parathyroid hormone, carcinoembryonic antigen (CEA), phosphohexose isomerase, ceruloplasmin, plasminogen, cholinesterase, plasminogen activator inhibitor (PAI), complement C1, prealbumin, complement C1 Inhibitor, NTproBNP, complement C1Q, procalcitonin (PCT), complement C3, prolactin, complement C4, properdin factor B, complement C5, prostatic acid phosphatase (PAP), CRP, prostatic specific antigen (PSA), creatine kinase-BB (CKBB), protein C, creatine kinase-MM (CKMM), protein S, cystatin C, pseudocholinesterase, erythropoietin, pyruvate kinase, factor IX antigen, renin, factor X, retinol binding protein (RBP), factor XIII, sex hormone-binding globulin, ferritin, soluble mesothelin-related peptide, fibrinogen, sorbital dehydrogenase (SDH), fibronectin, thyroglobulin, FSH, TSH, GGT, thyroxine binding globulin (TBG), haptoglobin, tissue plasminogen activator (T-PA), human chorionic gonadotropin (hCG), transferrin, hemopexin, transferrin receptor (TFR), her-2/neu protein, troponin T (TnT), human growth hormone (HGH), Tnl (cardiac), human placental lactogen (HPL), trypsin, IgA, urokinase, IgD, Von Willebrand factor, IgE, nucleotidase, IgG subclass 4, ADAMTS13 activity and inhibitor, inhibin B (infertility), adenosine deaminase, IGFBP-2, adiponectin, intercellular adhesion molecule 1, a subunit of pituitary glycoprotein hormones, interferon-□, α-galactosidase, interferon-α, EIA, α-N-acetylglucosaminidase, interleukin-1 receptor antagonist, amyloid 13-protein, interleukin-1 soluble receptor type II, angiotensinogen, interleukin-1α, anti-Mullerian hormone (AMH), interleukin-113, 3-glucuronidase, interleukin-2, 3-N-acetylglucosaminidase, interleukin-3, calprotectin, interleukin-4, cancer antigen 72-4, interleukin-5 cholecystokinin, interleukin-6, complement C2, interleukin-7, complement C4 binding protein, interleukin-8, complement C6, interleukin-9, complement C7 level, interleukin-10, complement C8 level, interleukin-11, complement C9 level, interleukin-12, corticosteroid binding globulin (transcortin), interleukin-13, CYFRA 21-1 (soluble cytokeratin fragment), interleukin-14, dopa decarboxylase, interleukin-15, elastase, interleukin-16, eosinophil cationic protein, interleukin-17, epidermal growth factor, interleukin-18, epidermal growth factor receptor (EGFR), kallikrein, factor II, leptin, factor V, leucine aminopeptidase, factor VII, mannose-binding lectin, factor VIII, neuron-specific enolase (NSE), factor XI, neurophysin, factor XII, pancreastatin, fibroblast growth factor (FGF2), pepsinogen I, gastric inhibitory polypeptide (GIP), pepsinogen II, Glial cell-derived neurotrophic factor (GDNF), glutathione peroxidase, proteasome activity, plasma-based Leumeta, granulocyte colony-stimulating factor, S-100B protein, granulocyte-macrophage colony-stimulating factor, soluble CD30, growth hormone binding protein, squamous cell carcinoma antigen, hemoglobin, thyrotropin releasing hormone (TRH), heparin cofactor II, transforming growth factor-131, hexosaminidase A and total hexosaminidase, tumor necrosis factor receptor 1, high molecular weight kininogen, tumor necrosis factor receptor 2, human growth hormone-releasing hormone (HGH-RH), tumor necrosis factor-α, IgG subclass 1, tumor necrosis factor-13, IgG subclass 2, vascular endothelial growth factor (VEGF), IgG subclass 3, and vitamin D-binding protein.

As would be apparent, the method may also be employed to identify a microbial (e.g., bacterial or viral) pathogen in a clinical sample, e.g., a cell surface protein or secreted protein. In these embodiments, the capture agents may target proteins or other moieties from a pathogen. If circles are detected, then the subject may be diagnosed as being infected by that pathogen. Microbes that might be identified using the present methods, compositions and kits include but are not limited to: viruses, yeast, Gram (+) bacteria, Gram (−) bacteria, bacteria in the family Enterobacteriaceae, bacteria in the genus *Enterococcus*, bacteria in the genus *Staphylococcus*, and bacteria in the genus *Campylobacter*, *Escherichia coli* (*E. coli*), *E. coli* of various strains such as, K12-MG1655, CFT073, O157:H7 EDL933, O157:H7 VT2-Sakai, etc., *Streptococcus pneumoniae, Pseudomonas aeruginosa, Staphylococcus aureus*, coagulase-negative staphylococci, a plurality of *Candida* species including *C. albicans, C. tropicalis, C. dubliniensis, C. viswanathii, C. parapsilosis, Klebsiella pneumoniae*, a plurality of *Mycobacterium* species such as *M. tuberculosis, M. bovis, M. bovis BCG, M. scrofulaceum, M. kansasii, M. chelonae, M. gordonae, M. ulcerans, M. genavense, M. xenoi, M. simiae, M. fortuitum, M. malmoense, M. celatum, M. haemophilum* and *M. africanum, Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

In some embodiments, the results of the method may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective). In some embodiments, the method may be used to analyze a group of 1, 2, 3, 4, 5, 6, 7, 8, 9 or 10 or more analytes that are independently either present at a higher concentration or lower concentration relative to a control (e.g., an internal control), where collectively the identity of the analytes and their abundance correlate with a phenotype.

The method may be used to analyze a patient sample. In this embodiment, the method may comprise: (a) quantifying, using the above-described method, one or more analytes in a sample and (b) providing a report indicating a correlation with phenotype. This embodiment may further comprise making a diagnosis, prognosis or theranosis based on the report. The report may indicate the normal range of the analyte.

In some embodiments, the method may involve creating a report as described above (an electronic form of which may have been forwarded from a remote location) and forwarding the report to a doctor or other medical professional to determine whether a patient has a phenotype (e.g., cancer, etc.) or to identify a suitable therapy for the patient. The report may be used as a diagnostic to determine whether the subject has a disease or condition, e.g., a cancer. In certain embodiments, the method may be used to determine the stage or type of cancer, to identify metastasized cells, or to monitor a patient's response to a treatment, for example.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information refers to transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or email transmissions and information recorded on websites and the like. In certain embodiments, the report may be analyzed by an MD or other qualified medical professional, and a report based on the results of the analysis of the image may be forwarded to the patient from which the sample was obtained.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device for performing a digital assay of a fluidic sample containing or suspected of containing an analyte, comprising:
   a first plate, a second plate, spacers, and microwells, wherein:
   (a) the first and second plates are movable relative to each other into an open configuration and a closed configuration, and comprise, on their respective inner surface, a sample contact area for contacting a fluidic sample that has a volume;
   (b) the second plate comprises, in the sample contact area, the microwells, wherein each microwell has (i) a predetermined and known geometry, (ii) a well depth of 200 μm or less, and (iii) a volume substantially less than the volume of the fluidic sample; and
   (c) the spacers are on one or both of the plates, wherein each spacer has a pillar shape and uniform height;
   wherein in the open configuration, an average spacing between an inner surface of the first plate and a rim of the microwells in the second plate is larger than the well depth, and the sample is deposited on one or both of the plates;
   wherein in the closed configuration, the inner surface of the first plate faces the inner surface of the second plate, at least a part of the sample is inside the microwells, and the height of the spacers is selected to make the average spacing between the inner surface of the first plate and the rim of the microwells in the second plate to be ½ (one half) of the microwell depth or less; and
   wherein the device further comprises second spacers that are configured to regulate the spacing between the first and second plates.

2. An apparatus comprising a thermal cycler and the device of claim 1.

3. An apparatus comprising a thermal cycler, the device of claim 1, and a reader for real-time PCR.

4. The device of claim 1, further comprising a binding site that is located on the sample contact area of one or both of the plates, wherein the binding site comprises a capture agent immobilized at the site, and the capture agent is configured to specifically capture the analyte in the sample.

5. The device of claim 1, further comprising a surface amplification layer that is located either on the sample contact area of one or both of the plates, wherein the surface amplification layer comprises a capture agent immobilized at the site, and the capture agent is configured to specifically capture the analyte in the sample, wherein the surface amplification layer amplifies an optical signal from the analyte or a label attached to the analyte when the analyte is in proximity of the surface amplification layer rather than a micron or more away.

6. The device of claim 5, wherein an amplification factor of the surface amplification layer is adjusted to make the optical signal from a single label that is bound directly or indirectly to the capture agent visible.

7. The device of claim 1, wherein device further comprise a reagent in the microwells in a close configuration of the second plate, wherein the reagent generates, when a detection agent specifically binds to the analyte, multiple light emitting components in the microwells.

8. The device of claim 1, wherein the average spacing in the closed configuration is configured to make saturation binding time of the analyte to the capture agents 300 sec or less.

9. The device of claim 1, wherein the average spacing in the closed configuration is configured to make saturation binding time of the analyte to the capture agents 60 sec or less.

10. The device of claim 5, wherein an amplification factor of the surface amplification layer is adjusted to make the optical signal from a single label visible.

11. The device of claim 4, wherein the capture agent is a nucleic acid.

12. The device of claim 4, wherein the capture agent is a protein.

13. The device of claim 4, wherein the capture agent is an antibody.

14. The device of claim 4, wherein the capture agent is an aptamer.

15. The device of claim 5, wherein the capture agent is an aptamer.

16. The device of claim 1, further comprising a storage site that is on the inner surface of one or both of the plates, wherein the storage site comprises a reagent dissolvable in a liquid.

17. The device of claim 7, wherein the reagent is a reagent for amplification of an analyte in the sample.

18. The device of claim 7, wherein the reagent amplifies the analyte by polymerase chain reaction (PCR).

19. The device of claim 7, wherein the reagent is a detection reagent.

20. The device of claim 1, wherein each microwell has a volume, and the volume of each microwell is configured, for an expected analyte concentration, so that the distribution of the analyte in each microwell that is filled with the sample follows Poisson distribution.

21. The device of claim 1, wherein each microwell has a volume, and the volume of each microwell is configured, for an expected analyte concentration, so that the distribution of analyte in each microwell that is filled with the sample is, on average, one analyte per every 2 microwells, 3 microwells, 5 microwells, 10 microwells, 20 microwells, 30 microwells, 50 microwells, 75 microwells, 100 microwells, 150 microwells, 200 microwells, 300 microwells, 500 microwells, 1000 microwells, 2000 microwells, 10000 microwells, or 100,000 microwells, or in a range of any two value.

22. The device of claim 1, wherein each microwell has a volume, and the volume of each microwell is configured for an expected analyte concentration, so that the distribution of analyte in each microwell that is filled with the sample is, on average, one analyte per every 10 microwells, 20 microwells, 30 microwells, 50 microwells, 75 microwells, or 100 microwells, or in a range of any two value.

23. The device of claim 1, wherein, in the closed configuration, the average spacing between the inner surface of the first plate and the rim of the microwells in the second plate is less than ½ (one half), ⅓, ⅕, ⅙, ⅐, 18, ⅑, ¹⁄₁₀, ¹⁄₁₁ (one eleventh), ¹⁄₂₀, ¹⁄₃₀, ¹⁄₄₀, ¹⁄₅₀, ¹⁄₁₀₀, ¹⁄₃₀₀, ¹⁄₅₀₀ of the microwell depth.

24. The device of claim 1, wherein, in the closed configuration, the inner surface of the first plate and the rim of the microwell in the second plate are in contact.

25. The device of claim 1, wherein, in the closed configuration, the average distance between two neighboring microwells is less than 5 nm, 10 nm, 30 nm, 50 nm, 100 nm, 200 nm, 500 nm, 1 μm, 2 μm, 5 μm, 10 μm, 20 μm, 50 μm, or 100 μm.

26. The device of claim 1, wherein the microwells have a shape selected from the group consisting of round, rectangle and hexagon, with lattice of square and/or hexagon.

27. The device of claim 1, wherein the microwells on the first plate have a period (average well to well center distance) of at least 1 nm, 10 nm, 100 nm, 500 nm, 1 μm, 5 μm, 50 μm, 500 μm, or 1 mm.

28. The device of claim 1, wherein the microwells on the second plate have a well size (average length or diameter) of 1 nm to 1 mm.

29. The device of claim 1, wherein the microwells on the second plate have a depth of at least 1 nm, 10 nm, 100 nm, 500 nm, 1 μm, 5 μm, 50 μm, 500 μm, or 1 mm.

30. The device of claim 1, wherein the microwells comprise (i) no metal coating (ii) metal coating on bottom thereof (iii) metal coating on side wall of the well or side of the pillar or (iv) metal coating on both bottom and side wall thereof.

31. The device of claim 30, wherein the metal is gold, aluminum, silver, copper, tin, or any combination thereof.

32. The device of claim 1, wherein the microwells have a well area, a ratio of the well area to a total area of the inner surface of the second plate is 40% to 50%, 50% to 60%, 60% to 70%, 70% to 80%, 80% to 90%, or 90% to 99%.

33. The device of claim 1, wherein each microwell has a well edge, and a distance between two neighboring well edges is larger than the well depth, which is to make sure a diffusion time from a well edge to another is longer than that from a well edge to a bottom of each microwell.

34. The device of claim 1, wherein the dimensions of the microwells are configured to make sure no cross-reaction takes place during the assay process.

35. The device of claim 1, wherein the microwells on the second plate outnumber the analyte in the sample.

36. The device of claim 1, wherein a total number of microwells on the second plate is 1 to 2 times, 2 to 5 times, 5 to 10 times, 10 to 100 times, 100 to 1000 times, 1000 to 10000 times of 600, if the molecule concentration is about 1 fM/uL.

37. The device of claim 1, wherein a total number of microwells on the second plate is 1 to 2 times, 2 to 5 times, 5 to 10 times, 10 to 100 times, 100 to 1000 times, 1000 to 10000 times of 600,000, if the molecule concentration is about 1 pM/uL.

38. The device of claim 1, wherein a total number of microwells on the second plate is 1 to 2 times, 2 to 5 times, 5 to 10 times, 10 to 100 times, 100 to 1000 times, 1000 to 10000 times of 600,000,000, if the molecule concentration is about 1 nM/uL.

39. The device of claim 1, wherein the number of microwells allows for no more than one target molecule being placed in a well after closing the device.

40. The device of claim 1, wherein at least one of the first and second plates comprises an amplification surface on the microwells.

41. The device of claim 1, wherein the device further comprises a sealer layer between the first plat and the second plate, wherein in the closed configuration, the sealer layer is configured to prevent the sample or the analyte in one microwell from moving to other microwells.

42. The device of claim 5, wherein the surface amplification layer comprises a layer of metallic material.

43. The device of claim 5, wherein the surface amplification layer comprises a layer of metallic material and a dielectric material on top of the metallic material layer, wherein the capture agent is on the dielectric material.

44. The device of claim 42, wherein the layer of metallic material is a uniform metallic layer, nanostructured metallic layer, or a combination thereof.

45. The device of claim 5, wherein the surface amplification layer comprises a layer of metallic material and a dielectric material on top of the metallic material layer, wherein the capture agent is on the dielectric material, and the dielectric material layer has a thickness of 0.5 nm to 500 μm.

* * * * *